United States Patent [19]

Lau et al.

[11] Patent Number: 4,667,032

[45] Date of Patent: May 19, 1987

[54] PHENOTHIAZONE DERIVATIVES AND ANALOGS

[75] Inventors: Cheuk K. Lau, Pierrefonds; Christiane Yoakim, Montreal; Joshua Rokach, Laval; Rejean Fortin, Montreal; Yvan Guindon, Ile Bizard, all of Canada

[73] Assignee: Merck Frosst Canada, Inc., Kirkland, Canada

[21] Appl. No.: 786,257

[22] Filed: Oct. 10, 1985

Related U.S. Application Data

[63] Continuation of Ser. No. 591,134, Mar. 19, 1984, abandoned, which is a continuation-in-part of Ser. No. 559,471, Dec. 12, 1983, abandoned, which is a continuation-in-part of Ser. No. 536,487, Sep. 28, 1983, abandoned, which is a continuation-in-part of Ser. No. 459,924, Jan. 22, 1983, abandoned.

[51] Int. Cl.$^4$ ............... C07D 265/38; C07D 279/18
[52] U.S. Cl. .................. 544/35; 544/14; 544/37; 544/99; 544/102; 544/103; 544/104
[58] Field of Search ............... 544/14, 35, 37, 99, 544/102, 103, 104; 260/112.5 R

[56] References Cited

U.S. PATENT DOCUMENTS

| | | | |
|---|---|---|---|
| 3,536,809 | 10/1970 | Applexweig | 424/28 |
| 3,598,123 | 8/1971 | Zaffaroni | 128/268 |
| 3,630,200 | 12/1971 | Higuchi | 128/260 |
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/260 |
| 4,343,398 | 9/1987 | Atkinson et al. | 424/258 |

FOREIGN PATENT DOCUMENTS 7322714 7/1973 Japan .

OTHER PUBLICATIONS

Terdic et al., Rev. Roum. Chim. 13 833 (1968).
Beckett et al., Xenobiotica 8 721 (1978).
Panea et al., Rev. Roum. Chim 25 691 (1980).
Bhargave et al., Gazz. Chim. Ital. 110 201 (1980).
Bodea et al., Ann. Chem. 698 186 (1966).
Sugita et al., Nippon Kagaku Zasshi 89 309 (1968).
Broser et al., Rev. Roum. Chim. 17 1745 (1972).
Bodea et al., Ann. Chem. 715 122 (1968).
Bodea et al., Rev. Roum. Chim 13 971 (1968).
Terdic et al., Rev. Roum. Chim 13 1241 (1968).
Tsujino Tet. Lett. (10) 763 (1969).
Roseboom et al., J. Pharm. Sci. 66 1395 (1977).
Fujisawa et al., Yakugaku Zasshi 86 541 (1966).
Bodea et al., Ann. Chem. 614 171 (1958).
McRae, Can. J. Med. Sci. 31 195 (1953).
Collier et al., Can. J. Med. Sci. 30 443 (1952).
Egan et al., Adv. Prost. Throm. Leuk. Res. 11 151 (1983).
Humes et al., J. Bio. Chem. 257 1591 (1982).
Winter et al., J. Pharm. Exp. Ther. 150 165 (1965).
Collier et al., Can. J. Biochem. 43 105 (1965).
Collier et al., Can. J. Biochem. 33 773 (1955).
Bailey et al., Ann. Rpts. Med. Chem. 16 213 (1981).
Baumann et al., Prostaglandins 20 627 (1980).
Collier et al., Can. J. Res. 20B 284 (1942).
Gordon et al., J. Counc. Sci. Ind. Res. (Aust.) 13 731 (1940).
Gallagher et al., Biochem. Pharm. 14 799 (1965).
Chemical Abstracts, vol. 72, No. 13, 3-30-70 p. 406 (Fujisawa).
Chemical Abstracts, vol. 90, No. 9, 2-26-79 p. 133 (Ghizdavu).
Chemical Abstracts, vol. 78, No. 7, 2-19-73 p. 485 (Shvedov).
Chemical Abstracts, vol. 92, No. 15, 4-14-80 p. 12 (Mitchell).
Journal of the Chem. Soc. Perkin Transactionsi, No. 3 (1982) (Gilchrist).
Chemical Abstacts, vol. 99, No. 9, 8-29-83 p. 622 (Raileanu).

*Primary Examiner*—Richard L. Raymond
*Attorney, Agent, or Firm*—Gabriel Lopez; Hesna J. Pfeiffer

[57] ABSTRACT

Phenothiazone derivatives and analogs thereof, pharmaceutical compositions and methods of treatment are disclosed. These compounds are useful as inhibitors of mammalian leukotriene biosynthesis. As such, these compounds are useful therapeutic agents for treating allergic conditions, asthma, cardiovascular disorders and inflammation.

22 Claims, No Drawings

PHENOTHIAZONE DERIVATIVES AND ANALOGS

CROSS REFERENCE TO RELATED APPLICATION

This is a continuation of application Ser. No. 591,134, filed Mar. 19, 1984, now abandoned, which is a continuation-in-part of copending application Ser. No. 559,471, filed Dec. 12, 1983, now abandoned which is a continuation-in-part of copending application Ser. No. 536,487, filed Sept. 28, 1983, now abandoned, which is a continuation-in-part of copending application Ser. No. 459,924, filed Jan. 22, 1983, now abandoned.

BACKGROUND OF THE INVENTION

This invention involves certain phenothiazone derivatives and analogs. These compounds are useful as inhibitors of mammalian leukotriene biosynthesis. As such, these compounds are useful therapeutic agents for treating allergic conditions, asthma, cardiovascular disorders and inflammation.

The leukotrienes are a novel group of biologically active mediators derived from arachidonic acid through the action of lipoxygenase enzyme systems. There are two groups of leukotrienes derived from the common unstable precursor Leukotriene A$_4$. The first of these are the peptido-lipid leukotrienes, the most important being Leukotrienes C$_4$ and D$_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene B$_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene B$_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., Ann. Rpts. Med. Chem. 17 203 (1982).

Respiratory Conditions (a) Asthma

The leukotrienes are potent spasmogens of human trachea, bronchus and lung parenchymal strips, and when administered to normal volunteers as aerosols are 3,000 times more potent that histamine at inducing a 50% decrease in air flow at 30% of vital capacity. They mediate increases in vascular permeability in animals and promote mucous production in human bronchial explants. In addition, Leukotriene B$_4$ may also mediate mucous production and could be an important mediator of neutrophil and eosinophil accumulation in asthmatic lungs. 5-Lipoxygenase products are also thought to be regulators of mast cell degranulation and recent studies with human lung mast cells have suggested that 5-Lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amounts of leukotrienes. There is therefore good evidence that the leukotrienes are important mediators of human asthma. 5-Lipoxygenase inhibitors would therefore be a new class of drugs for the treatment of asthma. See for example, B. Samuelson, Science 220 568-575 (1983).

Skin Diseases (a) Psoriasis

Psoriasis is a human skin disease which effects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene B$_4$ into human skin results in a pronounced neutrophil accumulation. There are gross abnormalities in arachiconic acid metabolism inhuman psoriatic skin. In particular, highly elevated levels of free arachidonic acid can be measured as well as large amounts of lipoxygenase products. Leukotriene B$_4$ has been detected in psoriatic lesions, but not in uninvolved skin, in biologically significant amounts.

Allergic Conditions (a) Leukotrienes can be measured in nasal washings from patients with allergic rhinitis and are greatly elevated following antigen challenge. Leukotrienes may mediate this disease through their ability to regulate mast cell degranulation, by modulating mucous production and mucocillary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes C$_4$ and D$_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function.

A number of Phenothiazone derivatives of the general Formula:

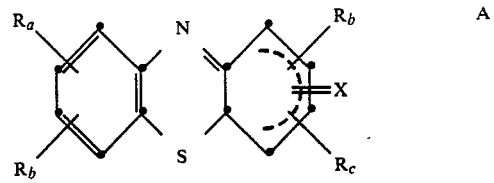

especially when X is O are taught in the literature; see for example Terdic et al., *Rev. Roum. Chim.* 13, 833–8 (1968; Beckett et al., *Xenobiotica* 8, 721-36 (1978); Panea et al., *Rev. Roum. Chim.* 25, 691–5 (1980); Bhargava et al.,; *Gazz. Chim. Ital.* 110, 201-3 (1980); Bodea et al., *Ann. Chem.* 698, 186-90, (1966); Sugita et al., *Nippon Kagaku Zasshi* 89, 309-15 (1968); Broser et al., *Rev. Roum. Chim.* 17, 1747-53 (1972); Bodea et al., *Ann.*

Chem. 715, 122-7 (1968); Bodea et al., *Rev. Roum. Chim.* 13, 971-6 1241-4 (1968); Sugita et al., Japanese Patent No. 73, 22,714 (1973); Tsyino, *Tet. Lett.* (10), 763-6 (1969); Roseboum et al., *J. Pharm. Sci.* 66, 1395-8 (1977); Shakii et al., Yakugaku Zasshi 86, 541-3 (1966); Bodea et al., *Ann. Chem.* 614, 171-6 (1958); Collier et al., *Can. J. Med. Sci.* 31, 195-201 (1953); and Collier et al., *Can. J. Med. Sci.* 30, 443-6 (1952). However, none of the compounds of Formula A are taught to have mammalian leukotriene biosynthesis inhibitor activity.

It has been discovered that compounds of Formula A and especially those where X is O are effective inhibitors of mammalian leukotriene biosynthesis and are thus useful therapeutic agents for treating conditions such as asthma, allergies, inflammation and certain skin diseases in humans.

SUMMARY OF THE INVENTION

This invention is directed to pharmaceutical compositions containing a compound of the Formula I:

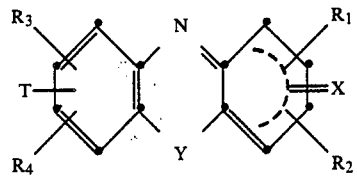

or a pharmaceutically acceptable salt thereof, a method of treatment using said composition and certain novel Formula I compounds.

DETAILED DESCRIPTION OF THE INVENTION

One embodiment of the present invention is a pharmaceutical composition containing a compound of the Formula I:

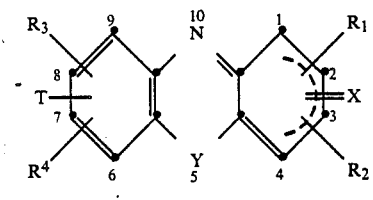

wherein

X is in the 1 or 3 position and is O, S or NR wherein R is H, $C_1$-$C_6$ branched or linear alkyl, CN or phenyl; Y is O, Se, S, SO, $SO_2$ or NR; and the broken line represents an optional double bond between the 1 and 2 or 2 and 3 position;

$R_1$, $R_2$, $R_3$ and $R_4$ are independently selected from:
(1) hydrogen;
(2) alkyl having 1-6 carbon atoms;
(3) alkenyl having 2-6 carbon atoms;
(4) —$(CH_2)_nM$ wherein n is 0-6 and M is
  (a) $OR_5$;
  (b) halogen;
  (c) $CF_3$;
  (d) $SR_5$ wherein $R_5$ is H; lower alkoxy-lower alkyl; lower acyloxy-lower alkyl; $C_1$-$C_6$ alkyl; benzyl; phenyl or substituted phenyl wherein the substituents are $C_1$-$C_3$ alkyl, halogen, CN, $CF_3$, $COOR_6$, $CH_2COOR_6$, $(CH_2)_nNR_8R_9$ wherein n is 0 to 2, $C_1$-$C_3$ alkoxy, OH, halo-$C_1$-$C_6$-alkyl; —$(CH_2)_mCOOR_6$, wherein m is 0 to 6 and $R_6$ is H, phenyl, or $C_1$-$C_6$ alkyl; CN; formyl; perfluoroalkyl; or $CH_2$-$R_{12}$ wherein n is 0 to 4, $R_{12}$ is $C_1$-$C_5$ alkyl, dimethylamino or phenyl;
  (e) phenyl or substituted phenyl as defined above for $R_5$;
  (f) $COOR_6$;
  (g)

wherein $R_{14}$ is H, $(CH_2)_nCOOR_6$ wherein n is 0 to 4, $C_1$-$C_6$ alkyl, $CF_3$, phenyl, or substituted phenyl as defined above for $R_5$;
  (h) tetrazole;
  (i)

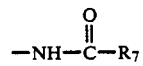

wherein $R_7$ is $C_1$-$C_6$ alkyl, benzyl or phenyl;
  (j) —$NR_8R_9$ wherein $R_8$ and $R_9$ are independently selected from H, phenyl or substituted phenyl as defined above for $R_5$, $C_1$-$C_4$ alkyl, $C_1$-$C_4$ alkylamino alkyl, or may be joined through the N to form a heterocycloalkyl of 5-8 ring atoms;
  (k) —$NHSO_2R_{10}$ wherein $R_{10}$ is OH, $C_1$-$C_6$ alkyl, $C_1$-$C_6$-alkoxy, phenyl, or $CF_3$;
  (l)

(m) —$SOR_{11}$ wherein $R_{11}$ is $C_1$-$C_6$ alkyl, phenyl or substituted phenyl as defined above for $R_5$, $(CH_2)_mCOOR_6$ wherein m is 1 to 6, CN, formyl or perfluoro-$C_1$-$C_4$ alkyl;
  (n) —$CONR_8R_9$;
  (o) —$SO_2NR_8R_9$;
  (p) —$SO_2R_{13}$ wherein $R_{13}$ is OH, $C_1$-$C_6$ alkyl, H, phenyl or substituted phenyl as defined above for $R_5$, $(CH_2)_mCOOR_6$ wherein m is 1 to 6, CN, formyl or perfluoro-$C_1$-$C_4$ alkyl;
  (q) $NO_2$;
  (r)

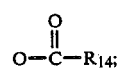

(s)

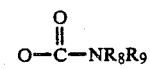

(t)

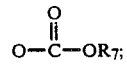

(u) CN;
  (v) $NR_{15}R_{16}$ wherein $R_{15}$ and $R_{16}$ are such that $HNR_{15}R_{16}$ is an essential amino cid; or any two of $R_1$, $R_2$, $R_3$ and $R_4$ are joined (e.g. as —$(CH_2)_{3-4}$—) to add a fourth ring to the three ring structure, said ring having 5 or 6 carbon atoms and being saturated or unsaturated; and, T is H, halogen or $CF_3$.

The numbers surrounding Formula I designate the substituent positions. T, $R_1$, $R_2$, $R_3$ and $R_4$ may be positioned anywhere in the structure. As an example of compounds with a fourth ring, compounds of Formula II may be prepared by linking two of the substituent groups; $R_1$, $R_2$, $R_3$, $R_4$:

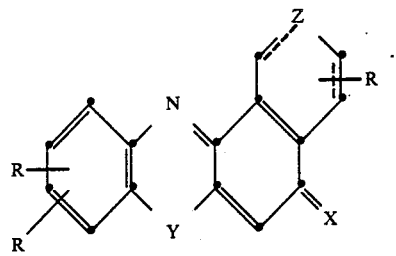

II wherein Z may be CH, $CH_2$ or a bond, the broken lines represent optional double bonds and R represents the substituent groups of Formula I ($R_1$, $R_2$, $R_3$, $R_4$ and/or T) not used to create the fourth ring.

The preferred compounds of Formula II have the structure II(a):

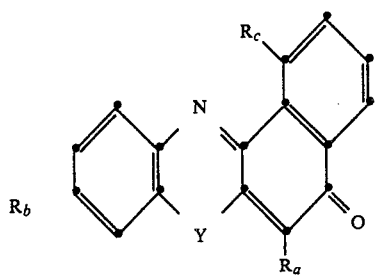

II(a)

wherein $R_a$ is selected from hydrogen, halogen (F, Br, Cl, I), $CH_3$, $CF_3$, $COR_d$, $NHR_d$, $SR_d$ and $OR_d$; $R_b$ is selected from hydrogen, halogen (F, Br, Cl, I), $CH_3$, $CF_3$, $CH_2OH$, $OR_d$, $SR_d$, $COR_d$, $COOR_d$, $CH_2COOR_d$ and $CH(CH_3)COOR_d$; $R_d$ is hydrogen, phenyl, $C_{1-4}$ straight or branched alkyl; $R_c$ is selected from hydrogen or $OR_d$; and Y is selected from O, S, SO or $SO_2$.

Pharmaceutically acceptable salts of the compounds described herein are included within the scope of the present invention. When the compounds os Formula I are acidic, such salts may be prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, tri-methylamine, diethanolamine, diethylamine, triethylamine, tripropylamine, ethanolamine, 2-dimethylaminoethanol, 2-diethylaminoethanol, tomethamine, lysine, arginine, histidine, caffeine, procaine, hydrabamine, choline, imidazole, betaine, ethylenediamine, glucosamine, methylglucamine, theobromine, purines, piperazine, N,N'-dibenzylethylenediamine, piperidine, N-ethylpiperidine, morpholine, N-ethylmorpholine, polyamine resins and the like.

When the compounds of Formula I are basic suitable acid additions salts may be prepared from pharmaceutically acceptable inorganic or organic acids, such as maleic, fumaric, succinic, acetic, isethionic, methanesulfonic, hydrochloric, hydrobromic, sulfuric or phosphoric acids and the like.

The term alkyl, unless indicated otherwise, includes straight chain, branched chain and cycloalkyl groups. The term halogen or halo, unless otherwise indicated, includes Cl, Br, I and F.

A group of preferred compositions contain a compound of the Formula:

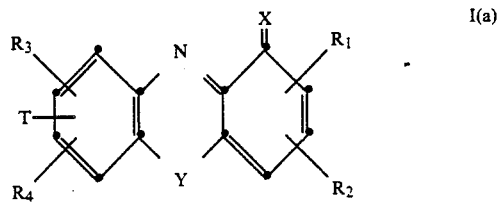

I(a)

More preferred Formula I(a) compounds are those wherein X is O or NH and Y is S, O, SO or $SO_2$. Still more preferred I(a) compounds are those having the formula:

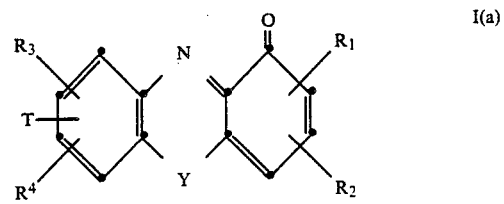

I(a)

wherein:
(a) T, $R_3$ and $R_2$ are hydrogens,
(b) T, $R_1$, $R_2$ are hydrogens,
(c) T, $R_3$ and $R_4$ are hydrogens,
(d) T, $R_1$, $R_2$ $R_3$ are hydrogens or
(e) T, $R_3$ $R_4$, $R_2$ are hydrogens. wherein $R_1$, $R_2$, $R_3$, $R_4$ and T are as defined for Formula I.

Another group of preferred compositions contain compounds of the Formula I(b):

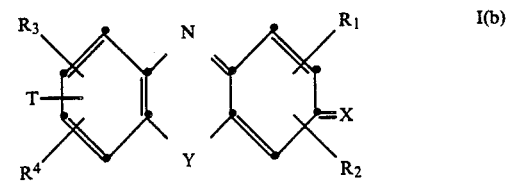

I(b)

More preferred compounds of Formula Ib are those having the Formula wherein X is O or NH and Y is O, S, SO, $SO_2$. Still more preferred compounds of Formula I(b) are those of the Formula I(c):

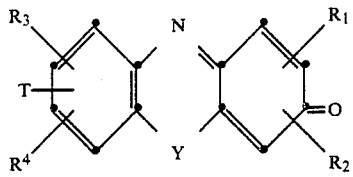

wherein:
(a) T, $R_3$ and $R_2$ are hydrogens,
(b) T, $R_1$, $R_2$ are hydrogens,
(c) T, $R_3$ and $R_4$ are hydrogens,
(d) T, $R_1$, $R_2$ $R_3$ are hydrogens,
(e) T, $R_3$ $R_4$, $R_2$ are hydrogens,
(f) T, $R_3$ and $R_4$ are hydrogens and $R_1$ is in position 4,
(g) T, $R_3$ $R_2$ are hydrogens and $R_1$ is in position 4,
(h) T, $R_4$, $R_3$ $R_2$ are hydrogens and $R_1$ is in position 4,
(i) $R_2$ and $R_3$ are hydrogens,
(j) $R_1$ and $R_2$ are hydrogens,
(k) $R_3$ and $R_4$ are hydrogens,
(l) $R_2$ $R_3$ are hydrogens and T is in position 4,
(m) T and $R_3$ are hydrogens and $R_2$ is in position 4,
(n) T and $R_3$ are hydrogens and $R_1$ is in position 4 and $R_2$ is in position 2,
(o) T and $R_3$ are hydrogens and $R_4$ is in position 7, $R_2$ is in position 4 and $R_1$ is in position 2.
(p) T is hydrogen, $R_1$, $R_2$, $R_3$, and $R_4$ are in positions 1, 2, 4 and 7, respectfully.

A particularly preferred series of Formula I(c) compounds are those in which n=0 or 1 in the unit —$(CH_2)_nM$.

Examples of Formula I compounds useful in the present compositions are tabulated below. In each of the tables the numbers preceding the T and the $R_1$–$R_4$ definitions indicate the substituent position in the structure. Standard abbreviations such as Me for methyl, Et for ethyl, Pr for propyl, Bu for butyl and Ph for phenyl are used.

TABLE 1

Compounds of the Formula

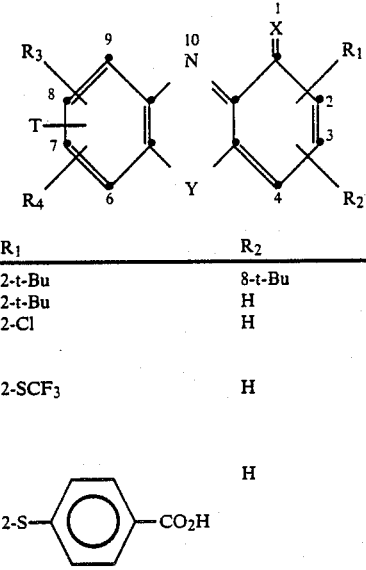

| Number | Y | X | $R_1$ | $R_2$ | $R_3$ | $R_4$ | T |
|---|---|---|---|---|---|---|---|
| 1 | O | O | 2-t-Bu | 8-t-Bu | 4-t-Bu | 6-t-Bu | H |
| 2 | O | O | 2-t-Bu | H | 4-Me | H | H |
| 3 | N—CH₃,S,O,Se,SO or SO₂ | O | 2-Cl | H | H | H | H |
| 4 | N—CH₃,S,O,Se,SO or SO₂ | O | 2-SCF₃ | H | H | H | H |
| 5 | N—CH₃,S,O,Se,SO or SO₂ | O | 2-S—⟨phenyl⟩—CO₂H | H | H | H | H |
| 6 | N—CH₃,S,O,Se,SO or SO₂ | O | 2-CN | H | H | H | H |
| 7 | N—CH₃,S,O,Se,SO or SO₂ | O | H | 3-CO₂Et | H | H | H |
| 8 | N—CH₃,S,O,Se,SO or SO₂ | O | H | 3-Cl | H | H | H |
| 9 | N—CH₃,S,O,Se,SO or SO₂ | O | H | H | 4-Cl | H | H |
| 10 | N—CH₃,S,O,Se,SO or SO₂ | O | H | H | 4-SO₂CH₃ | H | H |
| 11 | N—CH₃,S,O,Se,SO or SO₂ | O | 2-Cl | H | 4-Cl | H | H |
| 12 | N—CH₃,S,O,Se,SO or SO₂ | NH | 2-Cl | H | 4-Cl | H | H |
| 13 | N—CH₃,S,O,Se,SO or SO₂ | NH | H | H | H | H | H |
| 14 | N—CN | O | 2-Cl | H | 4-Cl | H | H |
| 15 | S | O | H | H | H | H | H |
| 16 | S | O | 2Cl | 3-Cl | 4-Cl | 7-Cl | 9-Cl |

TABLE 1-continued

Compounds of the Formula

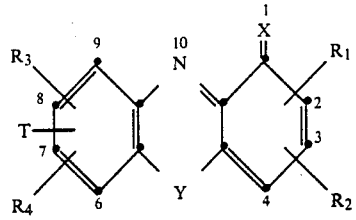

| Number | Y | X | R₁ | R₂ | R₃ | R₄ | T |
|---|---|---|---|---|---|---|---|
| 17 | S | O | 2-Br | 3-Br | 4-Br | 7-Br | 9-Br |
| 18 | S | O | H | H | H | 7-SO₂CH₃ | H |
| 19 | S | O | 2-Cl | H | 4-SO₂CH₃ | H | H |
| 20 | S | O | 2-F | H | 4-Cl | H | H |
| 21 | S | O | 2-Br | H | H | H | H |
| 22 | S | O | 2-CF₃ | H | H | H | H |
| 23 | S | O | 2-SCF₃ | H | H | H | H |
| 24 | S | O | 2-SO₂CF₃ | H | H | H | H |
| 25 | S | O | H | 3-Cl | H | H | H |
| 26 | S | O | H | 3-CO₂Et | H | H | H |
| 27 | S | O | H | 3-CO₂H | H | H | H |
| 28 | S | O | H | 3-CN | H | H | H |
| 29 | S | O | H | 3-SCF₃ | H | H | H |
| 30 | S | O | H | H | 4-Cl | H | H |
| 31 | S | O | H | H | 4-SCF₃ | H | H |
| 32 | S | O | H | H | 4-Cl | H | H |
| 33 | S | O | 2-Br | H | 4-Br | H | H |
| 34 | S | O | 2-Cl | H | H | 8-CN | H |
| 35 | S | O | 2-Cl | H | H | 8-CO₂Et | H |
| 36 | S | O | 2-Cl | H | H | 8-CO₂H | H |
| 37 | S | O | 2-Cl | H | H | 8-CF₃ | H |
| 38 | S | O | 2-Cl | H | H | 7-SO₂CH₃ | H |
| 39 | S | O | H | 3-CONMe₂ | H | H | H |
| 40 | S | O | 2-Cl | H | H | 7-OCH₃ | H |
| 41 | S | O | 2-S—C₆H₄—CO₂H | H | H | H | H |
| 42 | S | O | 2-SO₂CH₃ | H | H | H | H |
| 43 | S | O | 2-CH₂CH=CH₂ | H | 4-CH₂CH=CH₂ | H | H |
| 44 | S | O | H | 3-N(CH₃)₂ | H | H | H |
| 45 | S | O | H | H | 4-Cl | 7-S—C₆H₆ | H |
| 46 | S | O | 2-CH₂CO₂H | H | H | H | H |
| 47 | S | O | 2-Cl | H | 4-SCH₂CO₂H | 7-OCH₃ | H |
| 48 | S | O | 2-COCH₃ | H | 4-CO—C₆H₆ | 7-OCH₃ | H |
| 49 | S | O | H | H | 4-Cl | H | H |
| 50 | S | NH | 2-Cl | H | 4-Cl | H | H |
| 51 | S | NH | H | 3-N(CH₃)₂ | H | H | H |
| 52 | S | NH | 2-SCH₃ | H | 4-SCH₃ | H | H |
| 53 | S | O | H | H | H | H | H |
| 54 | S | NH | H | H | H | H | H |
| 55 | S | NH.HCl | H | H | H | H | H |
| 56 | S | O | H | H | H | H | H |
| 57 | O | O | H | H | H | H | H |
| 58 | O | NH | H | H | H | H | H |
| 59 | O | S | H | H | H | H | H |
| 60 | O | NH.HCl | H | H | H | H | H |
| 61 | Se | O | H | H | H | H | H |
| 62 | Se | NH | H | H | H | H | H |
| 63 | Se | S | H | H | H | H | H |
| 64 | NH | NH.HCl | H | H | H | H | H |
| 65 | NH | S | H | H | H | H | H |
| 66 | O | O | 4-Cl | H | 7-OMe | H | H |
| 67 | O | O | 4-Cl | H | H | H | H |
| 68 | O | O | 4-Me | H | H | H | H |
| 69 | O | O | H | 2-Cl | H | H | H |
| 70 | O | O | 4-Cl | 2-S—pPAA* | H | H | H |
| 71 | Se | O | 4-Cl | H | H | H | H |
| 72 | Se | O | 4-Cl | H | 7-OMe | H | H |
| 73 | Se | O | 4-Me | H | H | H | H |
| 74 | Se | O | 4-Cl | 2-S—pPAA* | H | H | H |
| 75 | N—CH₃ | O | 4-Cl | H | H | H | H |
| 76 | N—C₆H₆ | O | 4-Cl | H | 7-OMe | H | H |
| 77 | N—H | O | 4-Cl | 2-S—pPAA* | H | H | H |
| 78 | S | O | 4-Cl | H | H | H | H |

TABLE 1-continued

Compounds of the Formula

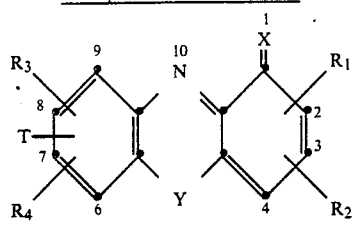

| Number | Y | X | R₁ | R₂ | R₃ | R₄ | T |
|---|---|---|---|---|---|---|---|
| 79 | SO | O | H | H | H | H | H |
| 80 | SO₂ | O | H | H | H | H | H |
| 81 | SO₂ | O | 4-Cl | H | H | H | H |
| 82 | N—Me | O | H | H | H | H | H |
| 83 | N—Me | O | 4-Cl | H | H | H | H |
| 84 | N—Me | O | 4-Cl | H | 7-OMe | H | H |
| 85 | N—Me | O | 4-Br | H | 7-OMe | 2-OMe | H |
| 86 | NCN | O | 4-Br | H | 7-OMe | 2-OMe | H |
| 87 | NCN | O | 4-Cl | H | H | H | H |
| 88 | NH | O | 2-Cl | H | H | H | H |
| 89 | NH | O | 4-Cl | H | H | H | H |
| 90 | S | O | 2-t-Bu | 4-t-Bu | H | H | H |
| 91 | S | O | 2-t-Bu | 4-t-Bu | 9-OMe | H | H |
| 92 | S | O | 2-t-Bu | 4-t-Bu | 7-F | H | H |
| 93 | S | O | 2-t-Bu | 4-t-Bu | 7-Me | H | H |
| 94 | S | O | 2-t-Bu | 4-t-Bu | 7-SMe | H | H |

*p-PAA = para-phenylacetic acid

TABLE 2

Compounds of the Formula

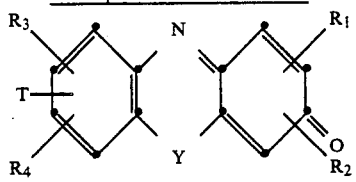

| Number | Y | R₁ | R₂ | R₃ | R₄ | T |
|---|---|---|---|---|---|---|
| 95 | S | H | H | H | H | H |
| 96 | S | 2-Cl | H | H | H | H |
| 97 | S | H | H | 6-Cl | H | H |
| 98 | S | H | H | 7-Cl | H | H |
| 99 | S | H | H | 8-Cl | H | H |
| 100 | S | H | H | 9-Cl | H | H |
| 101 | S | 1-Cl | H | H | H | H |
| 102 | S | 1-Cl | 4-Cl | H | H | H |
| 103 | S | 2-Cl | 4-Cl | H | H | 1-Cl |
| 104 | S | 2-N(Me)₂ | H | H | H | H |
| 105 | S | 2-SMe | H | H | H | H |
| 106 | S | 2-S—pPAA | H | H | H | H |
| 107 | S | 2-C(O)CH₃ | H | H | H | H |
| 108 | S | 2-OMe | H | H | H | H |
| 109 | S | H | H | H | 7-CH₂CO₂H | H |
| 110 | S | H | H | H | 8-CH₂COOH | H |
| 111 | S | H | 2-SO₃ | H | H | H |
| 112 | S | 2-N(Me)₂ | H | H | H | H |
| 113 | S | 2-SMe | H | H | H | H |
| 114 | S | 2-C(O)CH₃ | H | H | H | H |
| 115 | S | 2-OMe | H | H | H | H |
| 116 | S | 2-CH₂CO₂H | H | H | H | H |
| 117 | S | 2-CH(CH₃)CO₂H | H | H | H | H |
| 118 | S | 4-CH₂COOH | H | H | H | H |
| 119 | S | 4-CH(CH₃)CO₂H | H | H | H | H |
| 120 | S | H | H | 7-OH | 6-propyl | H |
| 121 | S | 4-Cl | H | H | H | H |
| 122 | S | 4-F | H | H | H | H |
| 123 | S | 4-F | H | 7-Cl | H | H |
| 124 | S | 4-Et | H | H | H | H |
| 125 | S | 4-Et | H | 7-OMe | H | H |
| 126 | S | 4-Et | H | 7-Cl | H | H |
| 127 | S | 4-Cl | H | 7-OMe | H | H |
| 128 | S | 4-OMe | H | 7-Cl | H | H |
| 129 | S | 4-Cl | H | 6-Cl | H | H |
| 130 | S | 4-Cl | H | 8-Cl | H | H |

TABLE 2-continued

Compounds of the Formula

| Number | Y | $R_1$ | $R_2$ | $R_3$ | $R_4$ | T |
|---|---|---|---|---|---|---|
| 131 | S | 4-Cl | H | 9-Cl | H | H |
| 132 | S | 4-Cl | H | 6-OMe | H | H |
| 133 | S | 4-Cl | H | 8-OMe | H | H |
| 134 | S | 4-Cl | H | 9-Et | H | H |
| 135 | S | 4-Cl | H | 6-Et | H | H |
| 136 | S | 4-Cl | H | 7-Et | H | H |
| 137 | S | 4-Cl | H | 8-Et | H | H |
| 138 | S | 4-Cl | 1-Et | H | H | H |
| 139 | S | 4-Cl | 2-Et | H | H | H |
| 140 | S | 4-Cl | 1-$CH_2COOH$ | H | H | H |
| 141 | S | 4-Cl | 2-$CH_2COOH$ | H | H | H |
| 142 | S | 4-Cl | H | 6-$CH_2COOH$ | H | H |
| 143 | S | 4-Cl | H | 7-$CH_2COOH$ | H | H |
| 144 | S | 4-Cl | H | 8-$CH_2COOH$ | H | H |
| 145 | S | 4-Cl | 2-$N(Me)_2$ | H | H | H |
| 146 | S | 4-Cl | 1-$N(Me)_2$ | H | H | H |
| 147 | S | 4-Cl | 2-$N(Me)_2$ | 7-OMe | H | H |
| 148 | S | 4-Cl | 2-$N(Me)_2$ | 7-Cl | H | H |
| 149 | S | 4-Cl | 2-SMe | H | H | H |
| 150 | S | 4-Cl | 2-$SCH_2COOH$ | H | H | H |
| 151 | S | 4-Cl | 2-S—pPAA | H | H | H |
| 152 | S | 4-Cl | 1-S—pPAA | H | H | H |
| 153 | S | 4-Cl | 2-S—pPAA | 7-OMe | H | H |
| 154 | S | 4-Cl | 2-$SO_3H$ | H | H | H |
| 155 | S | 4-Cl | 2-OMe | H | H | H |
| 156 | S | 4-Cl | 2-OMe | 7-Cl | H | H |
| 157 | S | 4-Cl | H | 7F | H | H |
| 158 | S | 4-OMe | H | 7-OMe | H | H |
| 159 | S | 4-OMe | H | 7-Me | H | H |
| 160 | S | 4-OMe | 2-SMe | H | H | H |
| 161 | S | 4-SMe | H | H | H | H |
| 162 | S | 4-Br | H | H | H | H |
| 163 | S | 4-I | H | H | H | H |
| 164 | S | 4-Br | H | 7-OMe | H | H |
| 165 | S | 4-I | H | 7-OMe | H | H |
| 166 | S | 4-Br | 2-Me | H | H | H |
| 167 | S | 4-I | 2-Me | H | H | H |
| 168 | S | 4-Cl | H | $\frac{7}{8}(CH_2)_4$— | | H |
| 169 | S | 4-Cl | H | $\frac{7}{8}(CH_2)_3$— | | H |
| 170 | S | 4-Br | 2-OMe | 7-OMe | H | H |
| 171 | S | 2-OMe | 7-OMe | H | H | H |
| 172 | S | 1-OMe | 7-OMe | H | H | 1-Br |
| 173 | S | 2-OMe | 7-OMe | H | H | 2-Br |
| 174 | S | 1-OMe | 7-OMe | H | H | 4-Br |
| 175 | S | 1-OMe | 7-Ome | H | H | 2-Cl |
| 176 | S | 1-OMe | 7-OMe | H | H | 4-Cl |
| 177 | S | 1-OMe | 7-OMe | H | H | 1-Cl |
| 178 | S | 2-OMe | 7-OMe | H | H | 4-Cl |
| 179 | S | 2-OMe | 7-OMe | H | H | 4-Cl |
| 180 | S | 2-OEt | 7-OEt | H | H | 1-Br |
| 181 | S | 2-OEt | 7-OEt | H | H | 4-Br |
| 182 | S | 2-OEt | 7-OEt | H | H | 1-Cl |
| 183 | S | 2-OEt | 7-OEt | H | H | 4-Cl |
| 184 | S | 2-OMe | 7-OMe | 8-OMe | H | 1-Br |
| 185 | S | 2-OMe | 7-OMe | 8-OMe | H | 4-Br |
| 186 | S | 2-OMe | 7-OMe | H | H | 4-F |
| 187 | S | 2-OMe | 7-Ome | H | H | 4-$CF_3$ |
| 188 | S | 2-OMe | 7-OEt | H | H | 4-Br |
| 189 | S | 2-OMe | 7-OEt | H | H | 4-Cl |
| 190 | S | 2-OMe | 7-OEt | H | H | 4-F |
| 191 | S | 2-OMe | 7-OEt | H | H | 4-$CF_3$ |
| 192 | S | 2-OEt | 7-OMe | H | H | 4-Br |
| 193 | S | 2-OEt | 7-OMe | H | H | 4-Cl |
| 194 | S | 2-OEt | 7-OMe | H | H | 4-F |
| 195 | S | 2-OEt | 7-OMe | H | H | 4-$CF_3$ |
| 196 | S | 1-OMe | 2-OMe | 7-OMe | H | 4-Br |
| 197 | S | 1-OMe | 2-OMe | H | H | H |
| 198 | S | 1-OMe | 2-OMe | H | H | 4-Br |
| 199 | O | | Same as Numbers 90–198 | | | |
| 200 | $SO_2$ | 4-OH | H | H | H | H |

TABLE 2-continued

Compounds of the Formula

| Number | Y | R$_1$ | R$_2$ | R$_3$ | R$_4$ | T |
|---|---|---|---|---|---|---|
| 201 | SO$_2$ | 1-OMe | 2-OMe | 4-CH$_3$ | H | H |
| 202 | SO$_2$ | 2-OMe | 7-OMe | 4-OH | H | H |
| 203 | SO$_2$ | 2-OMe | 4-OH | H | H | H |
| 204 | SO$_2$ | 1-OMe | 4-OH | H | H | H |
| 205 | SO$_2$ | 2-Me | 4-OH | H | H | H |
| 206 | SO$_2$ | 2-Cl | 4-OH | H | H | H |
| 207 | SO$_2$ | 2-OEt | 7-OEt | 4-OH | H | H |
| 208 | SO$_2$ | 2-SO$_2$Me | 4-OH | H | H | H |
| 209 | SO$_2$ | 4-OMe | H | H | H | H |
| 210 | SO$_2$ | 2-OMe | 4-OMe | 7-OMe | H | H |
| 211 | O | 1-CO$_2$H | 4-OH | 7-NMe$_2$ | H | H |
| 212 | O | 1-Cl | 2-Cl | 4-Cl | H | 7-Cl |
| 213 | S | 9-OMe | H | H | H | H |
| 214 | S | 2-OMe | H | H | H | H |
| 215 | S | 2-OMe | 4-OMe | H | H | H |
| 216 | S | 1-OMe | 2-OMe | 4-Me | H | H |
| 217 | S | 4-OMe | H | H | H | H |
| 218 | S | 1-OMe | 7-OMe | H | H | 4-Br |
| 219 | S | 1-OMe | 7-OMe | 2-Cl | H | 4-Cl |
| 220 | S | 1-OMe | 7-OMe | H | H | 4-Cl |
| 221 | S | 2-N⌒NMe | 7-OMe | H | H | H |
| 222 | S | 2-N⌒NMe | 7-OMe | H | H | 4-Br |
| 223 | SO$_2$ | 2-OMe | 4-OH | 7-OMe | H | H |
| 224 | SO$_2$ | 1-NHPr | 4-NHPr | H | H | H |
| 225 | SO$_2$ | 1-N⌒NMe | 4-N⌒NMe | H | H | H |
| 226 | SO$_2$ | 2-OMe | 4-N⌒NMe | 7-OMe | H | H |
| 227 | SO$_2$ | 2-OMe | 7-OMe | H | H | H |
| 228 | SO$_2$ | 2-OMe | 4-NHPr | 7-OMe | H | H |
| 229 | S | 1-NHPr | 4-NHPr | H | H | H |
| 230 | S | 1-NHPr | 4-NHPr | 7-OMe | H | H |
| 231 | S | 1-NHPr | 4-NHPr | H | H | H |
| 232 | S | 2-NHPr | 4-NHPr | 7-OMe | H | H |
| 233 | S | 2-OMe | 4-NH$_2$ | 7-OMe | H | H |
| 234 | S | 2-OMe | 4-NHPr | 7-OMe | H | H |
| 235 | O | 1-OMe | 4-Cl | 7-OMe | H | H |
| 236 | O | 1-OMe | 4-Br | 7-OMe | H | H |
| 237 | O | 1-NHPr | 4-NHPr | H | H | H |
| 238 | SO$_2$ | 1-OMe | 4-CN | 7-OMe | H | H |
| 239 | SO$_2$ | 2-OMe | 4-NHCH$_2$CO$_2$R* | 7-OMe | H | H |
| 240 | SO$_2$ | 2-OMe | 4-S—7-Bu | 7-OMe | H | H |
| 241 | SO$_2$ | 2-OMe | 4-CH$_2$CO$_2$R* | 7-Ome | H | H |
| 242 | SO$_2$ | 2-OMe | 4-SO$_2$Me | 7-OMe | H | H |
| 243 | S | 2-S—n-Bu | H | H | H | H |
| 244 | S | 4-S—n-Bu | H | H | H | H |
| 245 | S | 2-Me | 4-S—n-Bu | H | H | H |
| 246 | S | 2-OMe | 7-Me | H | H | 4-Br |
| 247 | S | 2-OMe | 7-CF$_3$ | H | H | 4-Br |

TABLE 2-continued

Compounds of the Formula

| Number | Y | $R_1$ | $R_2$ | $R_3$ | $R_4$ | T |
|---|---|---|---|---|---|---|
| 248 | S | 2-OMe | 7-F | H | H | 4-Br |
| 249 | S | 2-OMe | 7-Cl | H | H | 4-Br |
| 250 | S | 2-OMe | 7-Br | H | H | 4-Br |
| 251 | S | 2-OMe | 7-NMe$_2$ | H | H | 4-Br |
| 252 | S | 2-OMe | 7-SMe | H | H | 4-Br |
| 253 | S | 2-OMe | 7-SO$_2$Me | H | H | 4-Br |
| 254 | S | 2-OMe | 7-Ph | H | H | 4-Br |
| 255 | S | 1-Me | H | H | H | H |
| 256 | S | 2-Me | H | H | H | H |
| 257 | S | 2-OEt | H | H | H | H |
| 258 | S | 7-Cl | H | H | H | H |
| 259 | S | 9-Cl | H | H | H | H |
| 260 | S | 7-F | H | H | H | H |
| 261 | S | 7-Me | H | H | H | H |
| 262 | S | 7-OMe | H | H | H | H |
| 263 | S | 2-Cl | H | H | H | H |
| 264 | S | 1-Me | 7-Me | H | H | H |
| 265 | S | 1-Me | 7-Me | H | H | H |
| 266 | S | 2-OMe | 7-OEt | H | H | H |
| 267 | O | 2-NH$_2$ | H | H | H | H |
| 268 | O | 7-OH | H | H | H | H |
| 269 | O | COMe | H | H | H | H |
| 270 | SO$_2$ | 2-OMe | 7-OMe | H | H | 4-Br |
| 271 | S | 2-NHPr | 4-NHPr | H | H | H |
| 272 | S | 2-Cl | H | H | H | 4-Cl |
| 273 | S | 1-Me | 7-Me | H | H | 4-Cl |

*R is H or C$_1$ to C$_4$ alkyl.

TABLE 3

Compounds of the Formula

| Example | Y | X | $R_3$ | $R_4$ | T |
|---|---|---|---|---|---|
| 1 | O | O | H | H | H |
| 2 | S | O | H | H | H |
| 3 | SO | O | H | H | H |
| 4 | SO$_2$ | O | H | H | H |
| 5 | SO | O | H | H | 6-Cl |
| 6 | S | O | 6-COCH$_3$ | H | H |
| 7 | S | O | 6-CH$_3$ | H | H |
| 8 | SO$_2$ | O | 6-OH | H | H |
| 9 | SO$_2$ | O | 6-OMe | H | H |
| 10 | S | O | 9-OMe | H | H |
| 11 | S | O | 6-OH | H | H |
| 12 | S | O | 6-OMe | H | H |
| 13 | S | O | 6-NHCOMe | H | H |
| 14 | S | O | 6-NHPh | H | H |
| 15 | S | O | H | H | 6-Br |
| 16 | S | O | 6-NHMe | H | H |
| 17 | S | O | 6-NH—t-Bu | H | H |
| 18 | S | O | 6-NH—COMe | H | 9-Cl |
| 19 | S | O | 6-NH—COMe | 9-OMe | H |
| 20 | S | O | 6-NHPh—p-Br | H | 9-Cl |
| 21 | O | O | H | H | 6-Cl |
| 22 | O | O | H | H | 6-Br |
| 23 | O | O | 9-OMe | H | 6-Br |
| 24 | O | O | 9-OMe | 6-NHPr | H |
| 25 | S | O | 6-CF$_3$ | H | H |
| 26 | S | O | 6-S—n-Bu | H | H |
| 27 | S | O | 6-OMe | H | 9-Cl |
| 28 | S | O | 9-OMe | H | 6-Cl |
| 29 | S | O | 6-OMe | 9-OMe | H |
| 30 | S | O | 6-Cl | 9-Me | 11-Br |
| 31 | S | O | 6-NHPh | 9-Me | 11-Br |
| 32 | S | O | 6-Me | H | H |
| 33 | O | NH | 9-NMe$_2$ | 10-Me | H |
| 34 | O | NH | 9-N(Et)$_2$ | H | H |

The compounds of the Formula I have unexpected activity as inhibitors of the mammalian biosynthesis of leukotriene B$_4$, as well as leukotrienes C$_4$, D$_4$, E$_4$ and F$_4$, the active elements of the slow reacting substance of anaphylaxis (SRS-A). The compounds of Formula I act as inhibitors of the mammalian 5-Lipoxygenase enzyme system of the arachidonic acid cascade. This inhibition of the mammalian biosynthesis of leukotrienes indicates that the compositions would be useful to treat, prevent or ameliorate, in mammals and especially in humans (1) pulmonary conditions including diseases such as asthma, (2) allergies and allergic reactions such as allergic rhinitis, contact dermatitis, allergic conjunctivitis and the like, (3) inflammation such as arthritides, (4) pain, (5) skin conditions such as psoriasis and the like and (6) cardiovascular conditions such as angina and the like.

Representative compounds of Formula I have been tested using one or more of the following assays to determine their mammalian leukotriene biosynthesis inhibiting activity and other relevant activities.

RBL-1 5-Lipoxygenase

Rat basophilic leukemia (RBL-1) cells were sonicated and centrifuged at 125000 xg. The resulting supernatant fraction was incubated with arachidonic acid (labelled with $^{14}$C) to convert a portion of it to $^{14}$C-5(S)-hydroxyicosatetraenoic acid (5-HETE). Compounds being evaluated as inhibitors of 5-Lipoxygenase were added prior to the addition of arachidonic acid. 5-HETE was isolated by extraction and paper chromatography, and quantitated by determining the amount of radioactivity (cpm) associated with 5-HETE.

Reference: Egan, R. W., Tischler, A. M. Baptista, E. H., Ham, E. A., Soderman, D. D., and Gale, P. H., *Advances in Prostaglandin, Thromboxane and Leukotriene Research* 11 151 (1983), (Samuelson, B., Ramwell, P. W., and Paoletti, R. (eds.), Raven Press, N.Y.

Mouse Macrophage Assay

Mouse peritoneal macrophages were treated sequentially with arachidonic acid (labelled with tritium); the compound being evaluated as an inhibitor, and a stimulator (zymosan). Metabolites derived from arachidonic acid $PGE_2$, 6-keto $PH-F_{1\alpha}$ and leukotriene $C_4$ were separated from the incubation medium by extraction and chromatography, and then quantitated by determining the amount of radioactivity (cpm) associated with each of them. Inhibitors caused a reduction in the amount of radioactivity (cmp) associated with a given metabolite. (This protocol is identical to that described in the reference except that the radioactivity herein associated with the $LTC_4$ was determined by counting an aliquot of the final aqueous solution directly rather than chromatographing it first).

Reference: Humes, J. L. et al., *J. Biol. Chem.* 257, 1591–4, (1982).

Antigen Challenge 'in vitro' Assay

Male guinea pigs weighing 300–350 g were sensitized by injecting (I.P.) 0.5 ml of a suspension containing 0.4 mg of egg albumin (Ovalbumin, Grade V, Sigma Chemical Co.) and 4.0 g aluminum hydroxide in 19.6 ml of saline. Two weeks were permitted for sensitization to occur.

Three sensitized guinea pigs were stunned and exsanguinated. The tracheas were removed, freed of adhering tissue and divided longitudinally by cutting through the cartilaginous tissue directly opposite the muscle insertion. Each opened trachea was then transected between every second cartilage. Four of the cut sections were tied together, end to end, in a series with No. 7 silk thread ensuring that the tracheal muscles were all in the same vertical plane. Thus, each chain consisted of tissue from three different animals.

The chain so formed was then suspended under 1 g of tension (by silk ties at each end) in a 20 ml organ bath containing 10 ml of modified* Krebs-Henseleit buffer solution gassed with 95% $O_2$ and 5% $CO_2$ at 37° C. Mepyramine (0.55 μg/ml) and indomethacin (2.67 μg/ml) were added to the buffer to avoid the contribution of histamine receptors and cyclooxygenase products to the contraction. To record responses one end of the tracheal chain was attached to a Gould-Statham UC-2 force displacement transducer which was connected to a Beckman Type R-dynograph. The preparations were allowed to equilibrate for one hour during which time the tissues were automatically washed (10 ml volume displacement) every 6 minutes.

*modified Krebs solution in grams/liter and (mM): NaCl—6.87 (120); glucose—2.1 (11); NaHCO$_3$—2.1 (25); KCl—0.32 (4.72); CaCl$_2$—0.28 (2.5); MgSO$_4$.7H$_2$O—0.11 (0.5); KH$_2$PO$_4$—0.16 (1.2); pH at bathing solution=7.35±0.05.

After the equilibration period the tissues were primed with methacholine (3 μg/ml; $1.5\times10^{-5}$M), washed and allowed to recover to baseline. The tissues were treated again with a second dose of methacholine, washed, allowed to return to baseline and washed for an additional hour.

Two chains were used as a control. These were incubated in a concentration of egg albumin sufficient to induce an average contraction of 50–80% of the methacholine response.

Each compound to be tested was added to two other baths (at a final concentration in each bath of 10 μg/ml) 15 minutes prior to challenging the fresh chains with egg albumin.

The response of the challenged tissue was expressed as a percentage of the methacholine maximum. The % inhibition for each compound was then calculated. Compounds which at 10 μg/ml (final conc.) inhibited the egg albumin response by 50% or more were retested at a lower concentration.

Asthmatic Rat Assay

Rats were obtained from an inbred line of asthmatic rats. Both female and male rats from 200 to 300 g were used.

Egg albumin (EA), grade V, crystallized and lyophilized, was obtained from Sigma Chemical Co., St. Louis. *Bordetella pertussis* vaccine, containing $30\times10^9$ killed bacteria per ml was obtained from the Institut Armand-Frappier, Laval des Rapides, Quebec. Aluminum hydroxide was obtained from the Regis Chemical Company, Chicago.

The challenge and subsequent respiratory recordings were carried out in a clear plastic box with internal dimensions $10\times6\times4$ inches. The top of the box was removable; in use, it was held firmly in place by four clamps and an airtight seal was maintained by a soft rubber gasket. Through the center of each end of the chamber a Devilbiss nebulizer (No. 40) was inserted via an airtight seal and each end of the box also had an outlet. A Fleisch No. 0000 pneumotachograph was inserted into one end of the box and coupled to a Grass volumetric pressure transducer (PT5-A) which was then connected to a Beckman Type T Dynograph through appropriate couplers. While aerosolizing the antigen, the outlets were open and the pneumotachograph was isolated from the chamber. The outlets were closed and the pneumotachograph and the chamber were connected during the recording or the respiratory patterns. For challenge, 2 ml of a 3% solution of antigen in saline was placed into each nebulizer and the aerosol was generated with air from a small Potter diaphragm pump operating at 10 psi and a flow of 8 liters/minute.

Rats were sensitized by injecting (s.c.) 1 ml of a suspension containing 1 mg EA and 200 mg aluminum hydroxide in saline. Simultaneously, they received an injection (i.p.) of 0.5 ml of *B. pertussis* vaccine. They were used between days 14 and 18 postsensitization. In order to eliminate the serotonin component of the response, rats were pretreated intravenously 5 minutes prior to aerosol challenge with 30 gm/kg methylserzide. Rats were then exposed to an aerosol of 3% EA in saline for exactly 1 minute, then their respiratory profiles were recorded for a further 25-30 minutes. The duration of continuous dyspnoea was measured from the respiratory recordings.

Compounds were generally administered either intraperitoneally 1 hour prior to challenge or orally 1½ hours prior to challenge. They were either dissolved in dimethylsulfoxide or suspended in 0.1% methocel and 0.5% Tween 80. The volume injected has 2 ml/kg (intraperitoneally) or 10 ml/kg (orally). Prior to oral treatment rats were starved overnight. Their activity was determined in terms of their ability to decrease the duration of symptoms of dyspnoea in comparison with a group of vehicle-treated controls. Usually, a compound was evaluated at a series of doses and an $ED_{50}$ was determined. This was defined as the dose (mg/kg) which would inhibit the duration of symptoms by 50%.

PAF-Induced Hyperalgesia Assay

Female Sprague-Dawley rats, 35-40 g were fasted overnight. Platelet activating factor, PAF, (L-lecithin B-acetyl O-alkyl) 1 μg/0.1 ml was given by subplantar injection in the rat paw. The compounds to be evaluated were homogenized in Aqueous Vehicle (0.9% benzyl alcohol, 0.5% Tween 80 and 0.4% methylcellulose) and administered orally in a volume of 0.1 ml, 30 minutes prior to PAF.

Animals were tested 1, 2, 3 and 4 hours after PAF administration. The vocalization threshold, defined as the pressure (mmHg) needed to evoke a squeak response, was recorded for both the injected and contralateral paw. No animal was subjected to pressure greater than 60 mmHg. Hyperalgesia is defined as a decrease in vocalization threshold as compared to a normal paw. Percent inhibition of hyperalgesia was calculated as the proportion of animals with vocalization thresholds greater than 200% of controls.

Brewer's Yeast Hyperalgesia Assay

The standard method* for yeast hyperalgesia was used. Female Sprague-Dawley rats, 35-40 g were fasted overnight. A 5% solution (volume 0.1 ml) of Brewer's yeast was injected into the rat paw. The compound was homogenized in aqueous vehicle and given orally 2 hours after yeast. Vocalization thresholds were recorded 1 hours after drug (3 hours after yeast). Percent inhibition of hyperalgesia was determined by the proportion of animals with vocalization thresholds greater than 25 mmHg.

*Winter, C. A. et al., *J. Pharm. Exp. Ther.* 150, 165-171 (1965).

Following is data obtained using these various assays with representative compounds of Formula I.

TABLE 4

| Test No. | Compound | Macrophage Ic50 (μg/ml) | RBL-1 Ic50 (μg/ml) | In Vitro Antigen Challenge Test μg/ml and % Inhibition |
|---|---|---|---|---|
| 1 | | 0.2 | 0.01 | 10 μg (100%)<br>1 μg (44%) |
| 2 | | 0.5 | 0.01 | 10 μg (68%) |
| 3 | | 0.2 | — | 10 μg (25%) |
| 4 | | 0.1 | 0.01 | 10 μg (100%)<br>1 μg (77%)<br>0.3 μg (42%) |

TABLE 4-continued

Assay Results

| Test No. | Compound | Macrophage Ic50 (mg/ml) | RBL-1 Ic50 (mg/ml) | In Vitro Antigen Challenge Test mg/ml and % Inhibition |
|---|---|---|---|---|
| 5 | [structure: phenothiazine with N, S, two Cl and =O] | 0.1–0.5 | 65% at 0.05 μg/ml | 10 μg (45%) |
| 6 | [structure: (Me)₂N-substituted phenothiazine with NH.HCl, N, CH₃] | 10% at 0.05 mg/ml | — | 10 mg (24%) |
| 7 | [structure: (Me)₂N-substituted phenothiazine with NH.HCl, N] | 15% at 0.5 mg/ml | — | 10 mg (37%) |
| 8 | [structure: H₂N-substituted phenothiazine with N, S, NH.HCl] | 33% at 0.1 mg/ml | — | — |
| 9 | [structure: phenothiazine with N, S, three Cl and =O] | 75% at 5 mg/ml | — | — |
| 10 | [structure: phenothiazine with N, S, =O, C₂H₅] | — | — | 10 mg (100%) |
| 11 | [structure: MeO-substituted phenothiazine with OMe, Br, =O] | 0.1 | — | 3 mg (23%) |
| 12 | [structure: naphtho-phenothiazine with N, S, =O] | 0.1 | — | 10 mg (55%) |

TABLE 4-continued
Assay Results
| | | | | | |
|---|---|---|---|---|---|
| 13 | 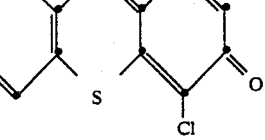 | — | — | 3 mg (54%) | |
| 14 | 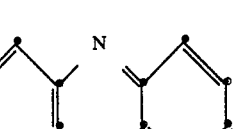 | 0.1 | — | — | |
TABLE 5
Asthmatic Rat Assay Results
| Test No. | Compound | Method of Administration | Ed$_{50}$ |
|---|---|---|---|
| A | 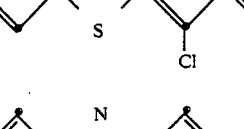 | i.p. | 0.5 mg/kg |
| B | | p.o. | 1.5 mg/kg |
| C | | i.p. | about 5.0 mg/kg |
| D | 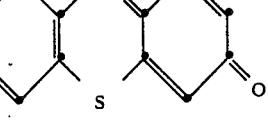 | p.o. | 1.0 μg/kg |
| E | 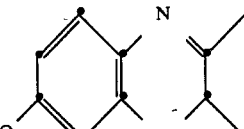 | p.o. | 37% inhibition at 1.5 mg/kg |

TABLE 5-continued

Asthmatic Rat Assay Results

| Test No. | Compound | Method of Administration | Ed$_{50}$ |
|---|---|---|---|
| F | (structure) | p.o. | 36% inhibition at 5 mg/kg |

TABLE 6

PAF-induced Hyperalgesia Assay for Compound of Example 2

| | Vocalization Threshold[a] | | % Inhibition |
|---|---|---|---|
| | Experiment 1 | | |
| 0.01 mg/kg p.o. | 28.2 | ± 5.2 | 40 |
| 0.03 | 40.2 | ± 5.0 | 80 |
| 0.1 | 37.4 | ± 3.9 | 80 |
| 0.3 | 45.4 | ± 3.7 | 90 |
| 3.0 | 46.0 | ± 3.0 | 100 |
| Control | 14.4 | ± 1.6 | |
| | Experiment 2 | | |
| 0.001 mg/kg p.o. | 10.0 | ± 1.6 | 0 |
| 0.003 | 16.4 | ± 2.8 | 30 |
| 0.01 | 18.0 | ± 2.9 | 30 |
| 0.1 | 29.6 | ± 4.4 | 60 |
| Control | 11.2 | ± 1.4 | |

[a] mmHg Mean ± S.E.M., n = 10 Reading taken 3 hr after injection of PAF, (3.5 hr. after administration of compound).

TABLE 7

Rat Brewer's Yeast Hyperalgesia Assay for Example 2 Compound

| Dose | Vocalization Threshold[a] | | % Inhibition |
|---|---|---|---|
| 0.3 mg/kg p.o. | 17.6 | 3.1 | 30 |
| 1.0 | 19.4 | 3.1 | 30 |
| 3.0 | 30.0 | 5.8 | 60 |
| 10.0 | 28.6 | 3.0 | 70 |
| 30.0 | 32.6 | 3.3 | 80 |
| Control | 10.2 | 1.3 | |

[a] mmHg: mean ± S.E.M. n = 10

The test results presented above show that representative compounds of Formula I inhibit the mammalian biosynthesis of leukotrienes especially via the 5-Lipoxygenase pathway of arachidonic acid metabolism and have representative pharmaceutical utility e.g., for asthma, pain and allergy.

The pharmaceutical compositions of the present invention will contain sufficient compound of Formula I in a dosage form suitable for inhibiting the mammalian biosynthesis of leukotrienes or, for the treatment desired. The effective concentration of the Formula I compound in the composition will vary as required by the mode of administration, dosage form and pharmacological effect and level desired. A general daily dosage of Formula I will range from about 10 μg to 20 mg/kg of body weight. This dosage may be administered in single or divided individual doses. More or less of the general daily dosage may be necessary depending upon the individual needs of the patient.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 μg to about 200 μg, administered as needed.

For treating allergies or allergic reactions, such as allergic conjunctivitis, allergic rhinitis and the like, the Formula I compound may be administered by any conventional mode, e.g., orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., are convenient dosage forms.

For use as an analgesic, i.e., for treating pain, any suitable mode of administration may be used, e.g., oral, parenteral, by insufflation, by suppository and the like.

For treating cardiovascular conditions such as angina pectoris, etc., any suitable mode of administration, e.g. oral, parenteral, topical, insufflation, etc. and dosage form e.g. pills, liquid formulations, controlled release capsules, controlled release skin patches, etc. may be used.

In addition to the common dosage forms set out above, the compound of Formula I may also be administered for the various utilities and indications or for inhibiting leukotriene synthesis by controlled release means and/or delivery devices such as those described in U.S. Pat. Nos. 3,845,770; 3,916,899; 3,536,809; 3,598,123; 3,630,200 and 4,008,719.

Dosage forms for application to treat the eye are also disclosed in U.S. Pat. No. 4,348,398.

In preparing suitable dosage forms, conventional compounding procedures and ingredients e.g. diluents, carriers, etc. may be used. The following are examples of representative pharmaceutical dosage forms:

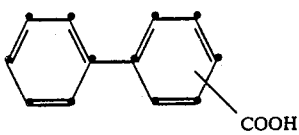

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

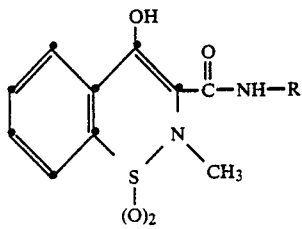

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodalac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, mictindole, nimesulide, orpanoxin, oxametacin, oxapadol, oxaprozin, perisoxal citrate, pimeprofen, pimetacin, piproxen, pirazolac, pirfenidone, pirprofin, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITC1, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent application Ser. No. 539,342, filed Oct. 5, 1983, Ser. No. 459,924, filed Jan. 21, 1983, Ser. No. 539,215, filed Oct. 5, 1983, and Ser. No. 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 81102976.8 and like compounds, such as those disclosed in U.S. Pat. Nos. 4,283,408; 4,362,736; 4,394,508; European Patent Application No. 40,696 and a pending application, U.S. Ser. No. 301,616, filed Sept. 14, 1981. The pharmaceutical compositions may also contain a K⁺/H⁺ ATPase inhibitor such as omeprazole, disclosed in U.S. Pat. No. 4,255,431, and the like. Each of the references referred to in this paragraph is hereby incorporated herein by reference.

The compound 2-S-glutathionyl-3H-phenothiazin-3-one or the compound 4-chloro-2-S-glutathionyl-phenothiazin-3-one may be substituted for a compound of the Formula I in the pharmaceutical compositions discussed above.

Another embodiment of the present invention are novel compounds encompassed by Formula I. These compounds have the Formula:

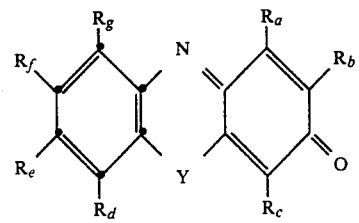

| Injectible Suspension | mg/mL |
|---|---|
| Compound of Example C | 1–100 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |
| Aerosol for Oral Inhibition | mg/can (200 doses/can) |
| Compound of Formula I | 2–40 |
| Oleic Acid | 0.2–4.0 |
| Trichloromonofluoro methane | 5,000–8,000 To a total |
| Dichloromonofluoro methane | 15,000–12,400 of 20,400 |
| Cream | mg/g |
| Compound of Formula I | 1–100 |
| Cetyl alcohol | 130.0 |
| Sodium Lauryl Sulfate | 15.0 |
| Propylene Glycol | 100.0 |
| Methyl paraben | 1.8 |
| Propyl paraben | 1.2 |
| Purified Water of sufficient quantity to make total 1 g | |
| Ointment | mg/g |
| Compound of Formula I | 1–100 |
| Methyl paraben | 1.8 |
| Propyl paraben | 1.2 |
| Petrolatum of sufficient quantity to make total 1 g | |
| Tablet | mg/table |
| Compound of Formula I | 0.2–350 |
| Microcrystalline Cellulose | 0–349.8 |
| Providone | 14.0 |
| Microcrystalline Cellulose | 90.0 |
| Pregelatinized Starch | 43.5 |
| Magnesium Stearate | 2.5 |
| | 500 |
| Capsule | mg/capsule |
| Compound of Formula I | 0.2–350 |
| Lactose Powder | 248.5–598.3 |
| Magnesium Stearate | 1.5 |
| | 600 |

In addition to the compounds of Formula I, the pharmaceutical compositions can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, and preferably from about 200:1 to about 1:200.

Combinations of a compound of the Formula I and other active ingredients will generally be within the aforementioned broad range and will preferably be within the aforementioned preferred range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/nonsteroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g. —CH$_2$COO$^-$Na$^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

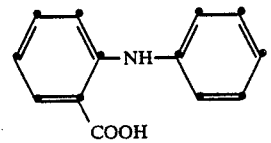

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

Tables 8 and 9 describe the novel compounds of the present invention:

TABLE 8
NOVEL FORMULA I COMPOUND

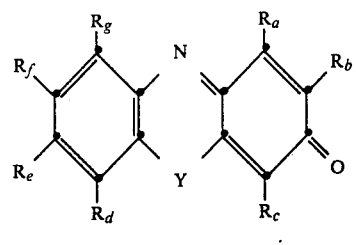

| Y | $R_a$ | $R_b$ | $R_c$ | $R_d$ | $R_e$ | $R_f$ | $R_g$ |
|---|---|---|---|---|---|---|---|
| S | H | H | $CF_3$ | H | H | H | H |
| S | H | $CF_3$ | $CF_3$ | H | H | H | H |
| S | $CF_3$ | H | H | H | H | H | H |
| S | H | F | H | H | H | H | H |
| S | H | $SCH_3$ | H | H | H | H | H |
| S | H | OH | H | H | H | H | H |
| S | H | H | $OCH_3$ | H | H | H | H |
| S | H | H | $SCF_3$ | H | H | H | H |
| S | H | H | CN | H | H | H | H |
| S | H | H | CHO | H | H | H | H |
| S | H | H | $COCF_3$ | H | H | H | H |
| S | H | H | H | H | $SCH_3$ | H | H |
| S | H | H | H | H | $OCH_3$ | H | H |
| S | H | H | H | H | $CO_2CH_3$ | H | H |
| S | H | H | H | H | $CO_2H$ | H | H |
| S | H | H | H | H | CN | H | H |
| S | H | H | H | H | CHO | H | H |
| S | H | H | H | H | $CONH_2$ | H | H |
| S | H | H | H | H | $CH_2OH$ | H | H |
| S | H | H | H | H | $CF_3$ | H | H |
| S | $CH_3$ | H | Cl | H | H | H | H |
| S | H | $CH_3$ | Cl | H | H | H | H |
| S | H | H | Cl | H | F | H | H |
| S | H | Cl | Cl | H | F | H | H |
| S | H | $CH_3$ | H | H | F | H | H |
| S | $CH_3$ | H | H | H | F | H | H |
| S | H | H | Cl | H | OMe | H | H |
| S | H | H | Cl | H | $CF_3$ | H | H |
| S | H | H | Cl | H | $CO_2Me$ | H | H |
| S | H | H | Cl | H | $CO_2H$ | H | H |
| S | H | H | Cl | H | CN | H | H |
| S | H | H | Cl | H | CHO | H | H |
| S | H | H | Cl | H | $CONH_2$ | H | H |
| S | H | H | Cl | H | $CH_2OH$ | H | H |
| S | H | H | $OCH_3$ | H | Cl | H | H |
| S | H | H | $CF_3$ | H | Cl | H | H |
| S | H | OEt | Cl | H | H | H | H |
| S | H | OiPr | H | H | H | H | H |
| S | OMe | H | Cl | H | H | H | H |
| S | OEt | H | Cl | H | H | H | H |
| S | H | OiPr | Cl | H | H | H | H |
| S | H | O—benzyl | Cl | H | H | H | H |
| S | H | $OCH_3$ | Cl | H | H | H | H |
| S | H | OEt | H | H | F | H | H |
| S | H | OEt | H | H | $CH_3$ | H | H |
| S | H | OEt | Cl | H | F | H | H |
| S | H | OEt | Cl | H | $CH_3$ | H | H |
| S | H | H | Cl | H | $CH_3$ | H | H |
| S | H | $CH_3$ | I | H | H | H | H |
| S | H | $CH_3$ | Br | H | H | H | H |
| S | $CH_3$ | H | H | H | $CH_3$ | H | H |
| S | H | $CH_3$ | H | H | $CH_3$ | H | H |
| S | $CH_3$ | H | Cl | H | $CH_3$ | H | H |
| S | H | $CH_3$ | Cl | H | $CH_3$ | H | H |
| S | Cl | H | Cl | H | F | H | H |
| S | H | OMe | Br | H | OMe | H | H |
| S | H | OMe | Cl | H | OMe | H | H |
| S | H | OEt | Br | H | OEt | H | H |
| S | H | OEt | Cl | H | OEt | H | H |
| S | H | OMe | Cl | H | OEt | H | H |
| S | H | OMe | H | H | SMe | H | H |
| O | H | OMe | Br | H | OMe | H | H |
| O | H | OMe | Cl | H | OMe | H | H |
| O | H | H | Cl | H | H | H | H |
| $SO_2$ | H | H | OH | H | H | H | H |

TABLE 8-continued
NOVEL FORMULA I COMPOUND

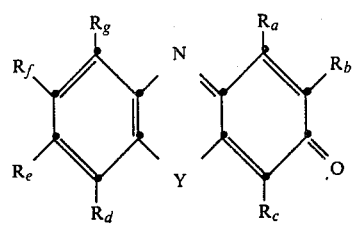

| Y | $R_a$ | $R_b$ | $R_c$ | $R_d$ | $R_e$ | $R_f$ | $R_g$ |
|---|---|---|---|---|---|---|---|
| $SO_2$ | H | OMe | OH | H | OMe | H | H |
| $SO_2$ | OMe | OMe | Me | H | H | H | H |
| $SO_2$ | H | H | OMe | H | H | H | H |
| $SO_2$ | H | OMe | OMe | H | OMe | H | H |
| S | H | H | H | H | H | H | $OCH_3$ |
| S | H | $OCH_3$ | H | H | F | H | H |
| S | H | $OCH_3$ | $OCH_3$ | H | H | H | H |
| S | $OCH_3$ | $OCH_3$ | Me | H | H | H | H |
| S | H | H | $COCH_3$ | H | H | H | H |
| S | $OCH_3$ | H | Br | H | $OCH_3$ | H | H |
| S | $OCH_3$ | Cl | Cl | H | $OCH_3$ | H | H |
| S | $OCH_3$ | H | Cl | H | $OCH_3$ | H | H |
| S | H | N⌒N—$CH_3$ | H | H | $OCH_3$ | H | H |
| S | H | N⌒N—$CH_3$ | Br | H | $OCH_3$ | H | H |
| $SO_2$ | H | $OCH_3$ | OH | H | $OCH_3$ | H | H |
| $SO_2$ | NHPr | H | NHPr | H | H | H | H |
| $SO_2$ | N⌒$NCH_3$ | H | N⌒$NCH_3$ | H | H | H | H |
| $SO_2$ | H | $OCH_3$ | N⌒$NCH_3$ | H | $OCH_3$ | H | H |
| $SO_2$ | H | $OCH_3$ | Br | H | $OCH_3$ | H | H |
| S | NHPr | H | NHPr | H | H | H | H |
| S | NHPr | H | NHPr | H | $OCH_3$ | H | H |
| S | H | NHPr | NHPr | H | H | H | H |
| S | H | NHPr | NHPr | H | $OCH_3$ | H | H |
| S | H | $OCH_3$ | $NH_2$ | H | $OCH_3$ | H | H |
| S | H | $OCH_3$ | NHPr | H | $OCH_3$ | H | H |
| $SO_2$ | H | $OCH_3$ | NHPr | H | $OCH_3$ | H | H |
| O | $OCH_3$ | H | Cl | H | $OCH_3$ | H | H |
| O | $OCH_3$ | H | Br | H | $OCH_3$ | H | H |
| O | NHPr | H | NHPr | H | H | H | H |
| $SO_2$ | H | $OCH_3$ | CN | H | $OCH_3$ | H | H |
| $SO_2$ | H | $OCH_3$ | $NHCH_2CO_2R$* | H | $OCH_3$ | H | H |
| $SO_2$ | H | $OCH_3$ | S—n-Bu | H | $OCH_3$ | H | H |
| $SO_2$ | H | $OCH_3$ | $CH_2CO_2R$* | H | $OCH_3$ | H | H |
| $SO_2$ | H | $OCH_3$ | $SO_2CH_3$ | H | $OCH_3$ | H | H |
| S | H | S—n-Bu | H | H | H | H | H |
| S | H | H | S—n-Bu | H | H | H | H |
| S | H | $CH_3$ | S—n-Bu | H | H | H | H |
| S | H | OMe | Br | H | $CF_3$ | H | H |
| S | H | OMe | Br | H | F | H | H |
| S | H | OMe | Br | H | Cl | H | H |
| S | H | OMe | Br | H | Br | H | H |
| S | H | OMe | Br | H | $NMe_2$ | H | H |
| S | H | OMe | Br | H | SMe | H | H |
| S | H | OMe | Br | H | $SO_2Me$ | H | H |
| S | H | OMe | Br | H | Ph | H | H |

TABLE 8-continued
NOVEL FORMULA I COMPOUND

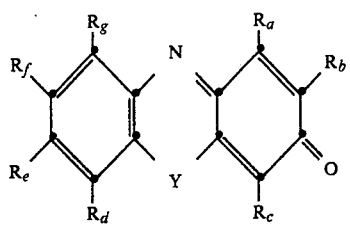

| Y | $R_a$ | $R_b$ | $R_c$ | $R_d$ | $R_e$ | $R_f$ | $R_g$ |
|---|---|---|---|---|---|---|---|
| S | H | H | H | Cl | OMe | H | H |
| S | H | OMe | Br | H | Me | H | H |

*R is H or $C_1$-$C_4$ alkyl.

Table 9 describes the novel compounds of the present invention having four rings.

TABLE 9
NOVEL COMPOUNDS OF FORMULA II

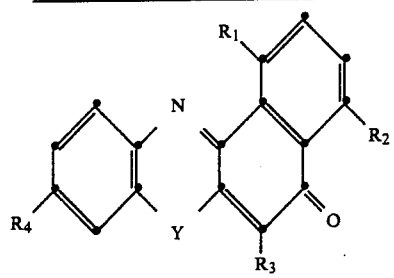

| Y | $R_1$ | $R_2$ | $R_3$ | $R_4$ |
|---|---|---|---|---|
| S | H | H | S—n-$C_4H_9$ | H |
| S | OH | H | $CH_3$ | H |
| S | $OCH_3$ | H | $CH_3$ | H |
| S | H | H | F | H |
| S | H | H | $CF_3$ | H |
| S | H | H | Cl | H |
| S | H | H | Cl | $CF_3$ |
| S | H | H | Cl | $SCH_3$ |
| S | H | H | Br | Cl |
| S | H | H | $CH_3$ | Br |
| S | H | H | F | Br |
| S | H | H | $COCH_3$ | Cl |
| S | H | H | $CF_3$ | $CH_3$ |
| S | H | H | S—n-$C_4H_9$ | $CH_3$ |
| S | H | H | $CF_3$ | Cl |
| S | H | H | Cl | *$CH_2COOR$ |
| S | H | H | Cl | *$CH(Me)CO_2R$ |
| S | H | H | Cl | $COCH_3$ |
| S | H | H | H | Cl |
| S | H | H | H | Br |
| S | H | H | H | F |
| S | H | H | H | $CF_3$ |
| S | H | H | H | $CH_3$ |
| S | H | H | H | $CH_2OH$ |
| S | H | H | H | $OCH_3$ |
| S | H | H | H | $SCH_3$ |
| S | H | H | H | *COOR |
| S | H | H | H | *$CH_2CO_2R$ |
| S | H | H | H | *$CH(Me)CO_2R$ |
| $SO_2$ | H | H | NHPr | H |
| $SO_2$ | H | H | 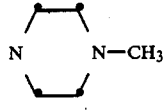 | H |
| $SO_2$ | H | H | $NH_2$ | H |
| $SO_2$ | H | H | NHPr | $OCH_3$ |
| S | —1,4-dihydro | | | H |
| S | H | H | NHPr | $OCH_3$ |
| O | H | H | Cl | H |

TABLE 9-continued
NOVEL COMPOUNDS OF FORMULA II

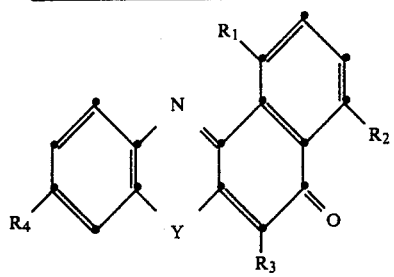

| Y | $R_1$ | $R_2$ | $R_3$ | $R_4$ |
|---|---|---|---|---|
| O | H | H | Br | H |
| O | H | H | Br | $OCH_3$ |
| O | H | H | NHPr | $OCH_3$ |

*R is H or $C_1$ to $C_4$ alkyl

Table 10 describes additional novel compounds of the present invention.

TABLE 10
NOVEL COMPOUNDS OF FORMULA I

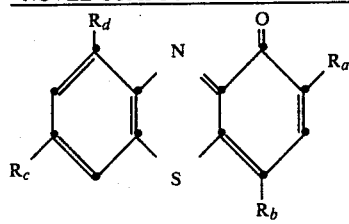

| $R_a$ | $R_b$ | $R_c$ | $R_d$ |
|---|---|---|---|
| t-Bu | t-Bu | H | H |
| t-Bu | t-Bu | F | H |
| t-Bu | t-Bu | Me | H |
| t-Bu | t-Bu | SMe | H |
| t-Bu | t-Bu | H | OMe |

Formula I includes both novel and known compounds. These compounds may be prepared by any process available to the skilled artisan.

One such process for compounds where X=O involves the oxidation of the appropriate phenothiazine as illustrated by the following equations.

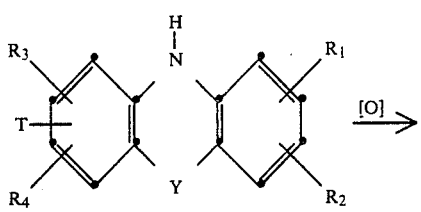

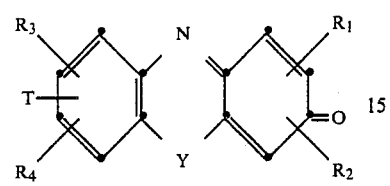

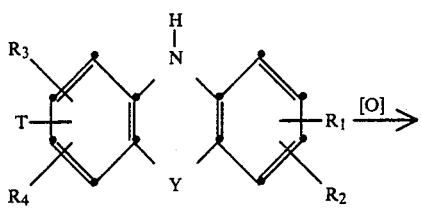

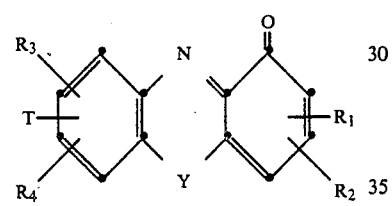

Various oxidizing agents and systems are taught in the art, e.g. $PbO_2$, $HNO_3$, $K_2Cr_2O_7$, $K_2Cr_2O_7$, iodine, $FeCl_3$ and the like.

Another process useful for preparing some Formula I compounds containing halogen substituents is by direct halogenation of an appropriate phenothiazone or analog thereof as illustrated by the following equation.

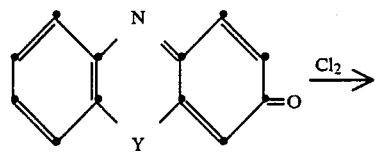

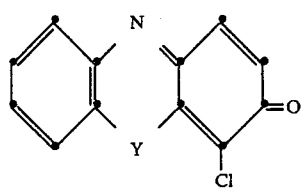

Still another process useful for preparing many of the Formula I compounds is by the reaction of an appropriate aniline with an appropriate quinone as illustrated by the following equation:

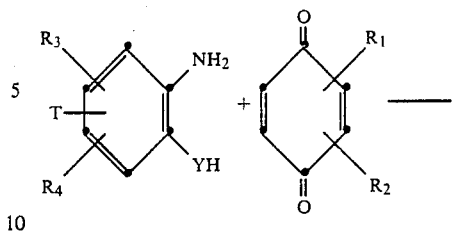

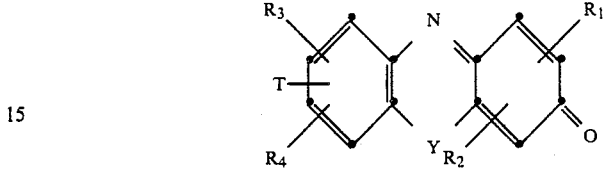

This general process is described in the literature.

A specific process for preparing the intermediate phenothiazin-3-one is illustrated by the following equation:

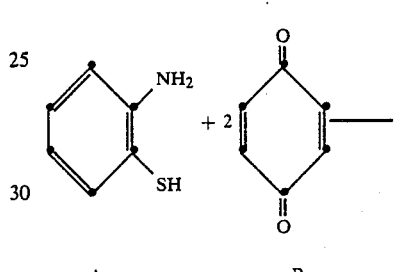

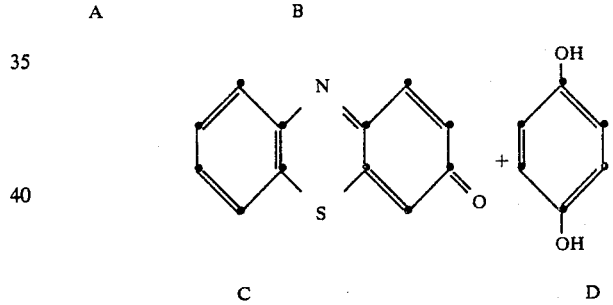

The process requires the use of 2 moles of quinone per mole of aniline. Any suitable solvent may be used. Example of such solvents are acetic acid, lower alkanols, acetic acid/$H_2O$, loweralkanol/water, other polar solvents and the like. A preferred solvent is one which will dissolve A, B and D and in which C is substantially insoluble. The reaction is readily carried out at room temperature—lower temperatures, e.g. as low as $-10°$ C., may be used—elevated temperatures may also be used but are not required. This process is more fully described in our copending application U.S. Ser. No. 459,923, filed on Jan. 21, 1983, which is hereby incorporated by reference.

Another useful process to prepare certain of the compounds of the present invention is the oxidation of certain phenothiazines or benzo[a]phenothiazines by standard oxidizing agents such as potassium dichromate, $NaClO_2$, 2,3-dichloro-5,6-dicyano-1,4-benzoquinone (DDQ), and the like. Several of these benzo[a]phenothiazines and phenothiazines are described in our copending applications U.S. Ser. Nos. 539,342 and 539,215, respectively, both filed on Oct. 5, 1983, which are hereby incorporated by reference.

Examples of the Formulae I and II compounds follow. These examples are provided merely as an aid to understand the instant invention. No limitation is intended, other than those that appear in the appended claims. All temperatures are in degrees Celsius and are uncorrected.

EXAMPLE 1

Method A

3H-Phenothiazin-3-one

To a stirring suspension of 1.72 kg (16 mol) of p-benzoquinone in 13 liters MeOH at room temperature was added slowly a solution of 1.0 kg (8 mol) of 2-aminothiophenol in 600 ml MeOH over a period of 1 hour. The resulting red mixture was stirred at room temperature for another 2 hours and then the product 3H-phenothiaz-3-one was filtered off. This 3H-phenothiazin-3-one was washed thoroughly with methanol and dried to give 1.07 kg of 3H-phenothiazin-3-one (61.49% yield), m.p. 157°–159° C.

Method B

To a stirring solution of 1.1 kg of ceric ammonium nitrate in 12.5 liters of $H_2O$ and 1.25 liters of HOAc at 10° C. was added dropwise a solution of 100 g of phenothiazine in 500 ml acetone over a period of 20 minutes. The resulting mixture was stirred for another 20 minutes and the product 3H-phenothiazin-3-one was then filtered off. The filtered 3H-phenothiazin-3-one was washed with water thoroughly and dried to give 92 g of crude 3H-phenothiazin-3-one. The crude 3H-phenothiazin-3-one was extracted with minimum volume of $CH_2Cl_2$. Upon dilution of the $CH_2Cl_2$ solution with 10 times the volume of cyclohexane, a precipitate was formed which was filtered and dried to afford 35 g of 3H-phenothiazin-3-one.

EXAMPLE 2

4-Chloro-3H-phenothiazin-3-one

To a stirring solution of 500 g (2.34 mol) of 3H-phenothiazin-3-one in 12.5 liters of glacial acetic acid was added 1.25 kg of potassium dichromate. The mixture was stirred at room temperature for ½ hour. To this resulting mixture was then added 2.34 mol of a 1M solution of chlorine in glacial acetic acid dropwise over a period of 4 hours. The progress of the reaction was monitored by tlc to ensure no excess chlorine was added. After addition of chlorine was completed the mixture was stirred at room temperature for another ½ hour and was then poured into 120 liters of $H_2O$ with vigorous stirring. The 4-chloro-3H-phenothiazin-3-one precipitated was allowed to settle overnight. The majority of the aqueous solution was siphoned and discarded and the rest was filtered. The filtered precipitate was washed thoroughly with water and then rinsed with methanol and was allowed to dry to give 504 g crude 4-chloro-3H-phenothiazin-3-one which was recrystallized from toluene, m.p. 221°.

EXAMPLE 3

4-Chloro-2,7-dimethoxy-3H-phenothiazin-3-one

Following the procedure described in Example 2 but substituting 2,7-dimethoxy-3H-phenothiazin-3-one for 3H-phenothiazin-3-one, the title compound was obtained, m.p. 264° C.

Analysis, calculated: C, 54.63; H, 3.27; N, 4.55; S, 10.42; Cl, 11.52. Observed: C, 54.64; H, 3.31; N, 4.53; S, 10.60; Cl, 11.69.

EXAMPLE 4

4-Chloro-1,7-dimethyl-3H-phenothiazin-3-one

Following the procedure described in Example 2 but substituting 1,7-dimethyl-3H-phenothiazin-3-one for 3H-phenothiazin-3-one for 3H-phenothiazin-3-one the title compound was obtained, m.p. 215°–218° C.

Analysis, calculated: C, 60.98; H, 3.66; N, 5.08; S, 11.63; Cl, 12.86. Observed: C, 60.78; H, 3.75; N, 4.99; S, 11.79; cl, 13.01.

EXAMPLE 5

4-Chloro-2,7-dimethyl-3H-phenothiazin-3-one

Following the procedure described in Example 2 but substituting 2,7-dimethyl-3H-phenothiazin-3-one for 3H-phenothiazin-3-one the title compound was obtained, m.p. 193°–195° C.

Analysis, calculated: C, 60.98; H, 3.66; N, 5.08; S, 11.63; Cl, 12.86. Observed: C, 60.89; H, 3.79; N, 5.22; S, 11.63; Cl, 12.50.

EXAMPLE 6

4-Chloro-2-methyl-3H-phenothiazin-3-one

Following the procedure described in Example 2 but substituting 2-methyl-3H-phenothiazin-3-one for 3H-phenothiazin-3-one, the title compound was obtained, m.p. 206° C.

Analysis, calculated: C, 59.66; H, 3.08; N, 5.35; S, 12.25; Cl, 13.55. Observed: C, 59.59; H, 3.35; N, 5.32; S, 12.64; Cl, 13.27.

EXAMPLE 7

4-Chloro-7-methyl-3H-phenothiazin-3-one

Following the procedure described in Example 2 but substituting 7-methyl-3H-phenothiazin-3-one for 3H-phenothiazin-3-one, the title compound was obtained, m.p. 218° C.

Analysis, calculated: C, 59.66; H, 3.08; N, 5.35; S, 12.25; Cl, 13.55. Observed: C, 59.48; H, 3.17; N, 5.27; S, 12.40; Cl, 13.63.

EXAMPLE 8

4-Chloro-7-ethoxy-2-methoxy-3H-phenothiazin-3-one

Following the procedure described in Example 2 but substituting 7-ethoxy-2-methoxy-3H-phenothiazin-3-one for 3H-phenothiazin-3-one, the title compound was obtained, m.p. 236°–239° C.

Analysis, calculated: C, 55.99; H, 3.76; N, 4.35; S, 9.96; Cl, 11.02. Observed: C, 56.05; H, 3.93; N, 4.37; S, 10.11; Cl, 10.99.

EXAMPLE 9

4-Bromo-2-methyl-3H-phenothiazin-3-one

Following the procedure described in Example 2 but substituting 2-methyl-3H-phenothiazin-3-one for 3H-phenothiazin-3-one and substituting bromine for chlorine, the title compound was obtained, m.p. 190° C.

Analysis, calculated: C, 50.99; H, 2.63; N, 4.57; S, 10.47; Br, 26.09. Observed: C, 50.97; H, 2.69; N, 4.61; S, 10.56; Br, 26.24.

EXAMPLE 10

9-Methoxy-3H-phenothiazin-3-one

To a suspension of p-benzoquinone (3.0 g) in 15 ml methanol was added 2-amino-3-methoxythiophenol (2.2 g) dissolved in 10 ml methanol. The mixture was stirred at room temperature for 45 minutes and concentrated in vacuo. The residue was triturated with ether and filtered. The resulting dark solid was chromatographed on silica gel and eluted with EtOAc, to afford the desired compound, m.p. 206°–207°.

Analysis, calculated: C, 64.18; H, 3.73; N, 5.76; S, 13.18. Observed: C, 64.10; H, 3.83; N, 5.69; S, 13.40.

EXAMPLE 11

7-Fluoro-3H-phenothiazin-3-oone

Following the procedure described in Example 10 but substituting 2-amino-5-fluorothiophenol for 2-amino-3-methoxythiophenol, the title compound was obtained, m.p. 240° C.

Analysis, calculated: C, 62.33; H, 2.61; N, 6.06; S, 13.86; F, 8.21. Observed: C, 62.26; H, 2.70; N, 6.05; S, 14.04; F, 8.06.

EXAMPLE 12

4-Chloro-7-fluoro-3H-phenothiazin-3-one

Following the procedure described in Example 2 but substituting 7-fluoro-3H-phenothiazin-3-one for 3H-phenothiazin-3-one, the title compound was obtained, m.p. 250°–255° C.

Analysis, calculated: C, 54.25; H, 1.90; N, 5.27; S, 12.07; F, 7.15; Cl, 13.34. Observed: C, 54.10; H, 2.01; N, 5.35; S, 12.20; F, 7.20; Cl, 13.50.

EXAMPLE 13

7-Fluoro-2-methoxy-3H-phenothiazin-3-one

Following the procedure described in Example 10 but substituting 2-amino-5-fluorothiophenol for 2-amino-3-methoxythiophenol and substituting 2-methoxy-p-benzoquinone for p-benzoquinone, the title compound was obtained, m.p. 252° C.

Analysis, calculated: C, 59.76; H, 3.08; N, 5.36; S, 12.27; F, 7.26. Observed: C, 59.60; H, 3.11; N, 5.20; S, 12.17; F, 7.33.

EXAMPLE 14

2,4-Dimethoxy-3H-phenothiazin-3-one

Following the procedure described in Example 10 but substituting 2-aminothiophenol for 2-amino-3-methoxythiophenol and substituting 2,6-dimethoxy-p-benzoquinone for p-benzoquinone, the title compound was obtained, m.p. 193° C.

Analysis, calculated: C, 61.52; H, 4.06; N, 5.12; S, 11.73. Observed: C, 61.37; H, 4.14; N, 5.16; S, 12.90.

EXAMPLE 15

1,2-Dimethoxy-4-methyl-3H-phenothiazin-3-one

Following the procedure described in Example 10 but substituting 2-aminothiophenol for 2-amino-3-methoxythiophenol and substituting 2,3-dimethoxy-5-methyl-p-benzoquinone for p-benzoquinone, the title compound was obtained, m.p. 138° C.

Analysis, calculated: C, 62.70; H, 4.56; N, 4.87; S, 11.16. Observed: C, 62.72; H, 4.74; N, 4.92; S, 11.28.

EXAMPLE 16

1,7-Dimethyl-3H-phenothiazin-3-one and 2,7-dimethyl-3H-phenothiazin-3-one

Following the procedure described in Example 10 but substituting 2-amino-5-methylthiophenol for 2-amino-3-methoxythiophenol and substituting 2-methyl-p-benzoquinone for p-benzoquinone, a mixture of the title compounds were obtained. Chromatography on silica gel eluting with 10% EtOAc in $CH_2Cl_2$ afforded firstly 2,7-dimethyl-3H-phenothiazin-3-one, m.p. 177° C.

Analysis, calculated: C, 69.70; H, 4.60; N, 5.81; S, 13.29. Observed: C, 69.51; H, 4.82; N, 5.78; S, 12.27, and secondly, 1,7-dimethyl-3H-phenothiazin-3-one. m.p. 168°–170° C.

Analysis calculated: C, 69.70; H, 4.60; N, 5.81; S, 13.29. Observed: C, 69.59; H, 4.63; N, 5.80; S, 13.40.

EXAMPLE 17

2,4-Dichloro-7-fluoro-3H-phenothiazin-3-one

Following the procedure described in Example 10 but substituting 2-amino-5-fluorothiophenol for 2-amino-3-methoxythiophenol and substituting 2,6-dichloro-p-benzoquinone for p-benzoquinone, the title compound was obtained, m.p. 256°–258° C.

Analysis, calculated: C, 48.02; H, 1.34; N, 4.68; S, 10.68; F, 6.33; Cl, 23.62. Observed: C, 47.93; H, 1.42; N, 4.63; S, 10.75; F, 6.42; Cl, 23.80.

EXAMPLE 18

1,4-Dichloro-7-fluoro-3H-phenothiazin-3-one

Following the procedure described in Example 10 but substituting 2-amino-5-fluorothiophenol for 2-amino-3-methoxythiophenol and substituting 2,5-dichloro-p-benzoquinone for p-benzoquinone, the title compound was obtained, m.p. 245°–247° C.

Analysis, calculated: C, 48.02; H, 1.34; N, 6.33. Observed: C, 48.20; H, 1.14; N, 6.20.

EXAMPLE 19

2-Methoxy-7-methylthio-3H-phenothiazin-3-one

Following the procedure described in Example 10 but substituting 2-amino-5-methylthio thiophenol for 2-amino-3-methoxythiophenol and substituting 2-methoxy-p-benzoquinone for p-benzoquinone, the title compound was obtained, m.p. 222°–224° C.

Analysis, calculated: C, 58.11; H, 3.83; N, 4.84; S, 22.16. Observed: C, 58.28; H, 4.24; N, 4.62; S, 22.02.

EXAMPLE 20

4-Trifluoromethyl-3H-phenothiazin-3-one and 2,4-bis(trifluoromethyl)-3H-phenothiazin-3-one A solution of 3H-phenothiazin-3-one (10 g), trifluoromethyl iodide (50 g) and pyridine (40 ml) in acetonitrile (140 ml) was irradiated with a 450 watt lamp for 3 days. The volatiles were removed under vacuum and the resulting residue chromatographed on a silica gel column eluting with 5% EtOAc/$CH_2Cl_2$ to afford firstly, 2,4-bis(trifluoromethyl)-3H-phenothiazin-3-one (650 mg) m.p. 173°–175° C.

Analysis, calculated: C, 48.14; H, 1.44; N, 4.01; S, 9.18; F, 32.64. Observed: C, 48.25; H, 1.72; N, 4.00; S, 9.28; F, 32.51.

Secondly, 4-trifluoromethyl-3H-phenothiazin-3-one (1.76 g), m.p. 184°–185° C.

Analysis, calculated: C, 55.51; H, 2.15; N, 4.98; S, 11.40; F, 20.27. Observed: C, 55.60; H, 2.14; N, 5.22; S, 11.43; F, 20.41.

EXAMPLE 21

4-Acetyl-3H-phenothiazin-3-one

A solution of 3H-phenothiazin-3-one (2 g) and acetaldehyde (32 ml) in benzene (240 ml) was irradiated with a 450 watt lamp for 2 days. The volatiles were removed under vacuum and the residue chromatographed on a silica gel column eluting with 25% EtOAc/hexane to afford the desired compound, m.p. 222° C.

Analysis, calculated: C, 65.87; H, 3.55; N, 5.49; S, 12.56. Observed: C, 65.88; H, 3.61; N, 5.30; S, 12.70.

EXAMPLE 22

4-Bromo-2,7-dimethoxy-3H-phenothiazin-3-one

Step 1: 2-Methoxy-p-benzoquinone

Vanillin (2.432 kg) was added to a solution of sodium hydroxide (640 g) in water (8 l) and cooled to 10° C. with an ice-bath. Then a solution of hydrogen peroxide (30%) (2.4 l) was added at a rate to keep the temperature of the reaction mixture below 30° C. The addition completed (about 2 hours), the reaction mixture was added over a period of 3 hours to a suspension of sodium periodate (880 g) in water (4 l) and acetic acid (640 ml) cooled with an ice-bath to 10° C. (the temperature of the reaction mixture was kept below 35° C.). The precipitate was filtered, washed with cold water followed by ethanol/hexane (1:1) mixture and air-dried to afford the title compound (1.9 kg), m.p. 144°-147° C.

Step 2: 2-Amino-5-methoxythiophenol

To a solution of potassium hydroxide 8N (1.3 l) was added 2-amino-6-methoxybenzothiazole (750 g) and the mixture was refluxed for 18 hours. The resulting solution was neutralized by the addition of concentrated HCl, to pH 8.0, then acetic acid to pH 6.0. The precipitate which formed was filtered and washed with water to afford the title compound which was used immediately in Step 3.

Step 3: 2,7-Dimethoxy-3H-phenothiazin-3-one

To a suspension of 2-methoxy-p-benzoquinone, (1.15 kg) (Step 1) in methanol (8 l) was added portionwise a suspension of 2-amino-5-methoxythiophenol (from Step 2) in methanol (6 l). The reaction mixture was stirred for 15 minutes at room temperature, filtered and the collected solid washed with methanol (8 l). The product isolated was swished with DMF (16 l) for 2 hours, filtered and air-dried. The crude material was dissolved in hot DMF (16 l) (130°-140° C.), filtered through Celite and the filtrate cooled to room temperature. The crystals were filtered, washed with methanol (8 l) and air-dried to afford the title compound (703 g), m.p. 237°-238° C.

Step 4: 4-Bromo-2,7-dimethoxy-3H-phenothiazin-3-one

A solution of bromine (280 g) in acetic acid (2.8 l) was added over a period of 30 minutes to a suspension of 2,7-dimethoxy-3H-phenothiazin-3-one (250 g) (Step 3) in acetic acid (7.5 l) and stirred for 2 hours. Methanol (12 l) was added and the mixture was stirred until the black suspension became an orange suspension. Then, the precipitate was filtered, washed with methanol and air-dried to afford the desired compound (312 g), m.p. 260°-261° C.

Analysis, calculated: C, 47.74; H, 2.86; N, 3.98; S, 9.10; Br, 22.69. Observed: C, 47.74; H, 2.81; N, 3.90; S, 9.02; Br, 22.37.

EXAMPLE 23

4-Chloro-2-ethoxy-3H-phenothiazin-3-one and 4-chloro-2,7-diethoxy-3H-phenothiazin-3-one Metallic sodium (506 mg) was dissolved in absorbed ethanol (75 ml) and 4-chloro-3H-phenothiazin-3-one (4.95 g) was added and stirred overnight at room temperature. The solvent was removed in vacuo, the resulting residue stirred in acetone (500 ml) for 1 hour and filtered. The filtrate was evaporated to dryness and the residue was chromatographed on a silica gel column eluting with 5% EtOAc/toluene to afford firstly, 4-chloro-2-ethoxy-3H-phenothiazin-3-one (1.33 g), m.p. 188°-189° C.

Analysis, calculated: C, 57.63; H, 3.45; N, 4.80; S, 10.99; Cl, 12.15. Observed: C, 57.66; H, 3.54; N, 4.81; S, 11.16; Cl, 12.02.

Secondly, 4-chloro-2,7-diethoxy-3H-phenothiazin-3-one (110 mg), m.p. 227°-228° C.

Analysis, calculated: C, 57.22; H, 4.20; N, 4.17; S, 9.55; Cl, 10.56. Observed: C, 57.19; H, 4.35; N, 4.07; S, 9.62; Cl, 10.61.

EXAMPLE 24

2-(n-Butylthio)-3H-phenothiazin-3-one

To a solution of 3H-phenothiazin-3-one (0.64 g) in 75 ml methanol was added triethylamine (1.0 ml) and n-butanethiol (0.58 ml). The mixture was stirred at room temperature for 48 hours. Then 2,3-dichloro-5,6-dicyano-1,4-benzoquinone (0.67 g) was added. The mixture was stirred at room temperature for 2 hours. The solvent was removed in vacuo. The residue was chromatographed on neutral alumina (Act III) and eluted with 15% EtOAc/hexane to afford the title compound (0.4 g), m.p. 133° C.

Analysis, calculated: C, 63.78; H, 5.02; N, 4.65 Observed: C, 63.61; H, 5.04; N, 4.51.

EXAMPLE 25

4-(n-Butylthio)-3H-phenothiazin-3-one

To a solution of phenothiazin-3-one (0.21 g) in 20 ml THF was added triethylamine (0.28 ml) and n-butanethiol (0.2 ml). The mixture was refluxed for 15 hours and then cooled to room temperature. 2,3-Dichloro-5,6-dicyano-1,4-benzoquinone (DDQ) (0.22 g) was added and the reaction was stirred for 2 hours at 25°. The solvent was removed in vacuo. The residue was chromatographed on neutral alumina (Act III) and eluted with 15% EtOAc/hexane to afford the title compound, m.p. 72° C.

Analysis, calculated: C, 63.78; H, 5.02; N, 4.05; S, 21.24. Observed: C, 63.83; H, 5.07; N, 4.86; S, 21.06.

EXAMPLE 26

4-(n-Butylthio)-2-methyl-3H-phenothiazin-3-one

To a solution of 2-methyl-phenothiazin-3-one (0.23 g) in 12 ml dichloroethane was added triethylamine (0.8 ml) and n-butanethiol (0.7 ml). The mixture was stirred at room temperature for 72 hours. 2,3-Dichloro-5,6-dicyano-1,4-benzoquinone (0.22 g) was added. The mixture was stirred at room temperature for 2 hours. The mixture was stirred at room temperature for 2 hours. The solvent was removed in vacuo and the residue was chromatographed on neutral alumina (Act III) eluting with 15% EtOAc/hexane to give the title compound (120 mg), m.p. 97° C.

Analysis, calculated: C, 64.75; H, 5.43; N, 4.44. Observed: C, 64.62; H, 5.53; N, 4.43.

EXAMPLE 27

2-S-Glutathionyl-3H-phenothiazin-3-one

A mixture of phenothiazin-3-one (0.22 g), triethylamine (0.41 ml) and glutathione (0.3 g) in 1,2-dichloroethane (12 ml) was stirred at room temperature for 5 days. The solvent was removed in vacuo. The residue was dissolved in water and filtered. The filtrate was concentrated in vacuo and then chromatographed on XAD resin and eluted with water to give the title compound.

EXAMPLE 28

4-Chloro-2-S-glutathionylphenothiazin-3-one

Following the procedure of Example 27, but substituting 4-chloro-3H-phenothiazine-3-one for 3H-phenothiazin-3-one, the title compound was obtained.

EXAMPLE 29

5H-Benzo[a]phenothiazin-5-one

Following the procedure described in Example 10 but substituting 2-aminothiophenyl for 2-amino-3-methoxythiophenyl and substituting 1,4-naphthoquinone for p-benzoquinone the title compound was obtained, m.p. 176°–177° C.

EXAMPLE 30

6-Chloro-5H-benzo[a]phenothiazin-5-one

Following the procedure described in Example 2, but substituting 5H-benzo[a]phenothiazin-5-one for 3H-phenothiazin-3-one, the title compound was obtained, m.p. 230°–231° C.

EXAMPLE 31

6-Methyl-5H-benzo[a]phenothiazin-5-one

Following the procedure described in Example 10, but substituting 2-aminothiophenol for 2-amino-3-methoxythiophenol and substituting 2-methyl-1,4-naphthoquinone for p-benzoquinone, the title compound was obtained, m.p. 181° C.

Analysis, calculated: C, 73.62; H, 4.00; N, 5.05; S, 11.56. Observed: C, 73.77; H, 4.16; N, 4.99; S, 11.69.

EXAMPLE 32

1-Hydroxy-6-methyl-5H-benzo[a]phenothiazin-5-one

Following the procedure described in Example 10 but substituting 2-aminothiophenol for 2-amino-3-methoxythiophenol and substituting 5-hydroxy-2-methyl-1,4-naphthoquinone for p-benzoquinone, the title compound was obtained, m.p. 226°–228° C.

Analysis, calculated: C, 69.61; H, 3.78; N, 4.77; S, 10.93. Observed: C, 69.66; H, 3.90; N, 4.66; S, 10.77.

EXAMPLE 33

1-Methoxy-6-methyl-5H-benzo[a]phenothiazin-5-one

Potassium tert.-butoxide (500 mg) was added to a suspension of 1-hydroxy-6-methyl-5H-benzo[a]phenothiazin-5-one (from Example 32) (500 mg) and methyl iodide (2 ml) in DMF (20 ml). After 30 minutes at room temperature, EtOAc (250 ml) was added followed by water (200 ml). The aqueous layer was decanted and the organic layer was dried and evaporated to dryness. The residue was treated with ether, filtered and air-dried to afford the desired product (420 mg), m.p. 170°–171° C.

Analysis, calculated: C, 70.34; H, 4.26; N, 4.56; S, 10.43. Observed: C, 70.37; H, 4.44; N, 4.45; S, 10.52.

EXAMPLE 34

4-Hydroxy-3H-phenothiazin-3-one-5,5-dioxide

To a suspension of 3-hydroxy-10H-phenothiazine-5,5-dioxide (1.75 g, 7 mmoles) in 2% aqueous sulfuric acid (25 ml) there was added, at room temperature, a solution of 80% sodium chlorite (3.17 g, 28 mmoles) in water (25 ml). The mixture was stirred for 15 minutes, then the red-orange precipitate was filtered to afford crude product (1.73 g). Purification was achieved by crystallization from DMF-methanol, m.p. 266° (dec.).

Analysis, calculated: C, 55.16; H, 2.70; N, 5.36; S, 12.27. Observed: C, 54.68; H, 2.76; N, 5.38; S, 12.47.

EXAMPLE 35

4-Chloro-3H-phenoxazin-3-one

To a solution of 1.2 g of 3H-phenoxazin-3-one in acetic acid (25 ml) was added $K_2Cr_2O_7$ (3.7 g). A solution of chlorine in acetic acid was added dropwise to the resulting suspension. After disappearance of the starting material, as monitored by TLC, the reaction mixture was poured into 200 ml of $H_2O$ and the resulting precipitate was filtered (1.2 g) and chromatographed on silica gel to yield the title compound.

Analysis, calculated: C, 62.22; H, 2.61; Cl, 15.30. Observed: C, 62.10; H, 2.75; Cl, 15.24.

EXAMPLE 36

2,4-Di-t-butyl-1H-phenothiazin-1-one

To a solution of 4.4 gm of 3,5-di-t-butyl-1,2-benzoquinone in 20 ml of ether was added a solution of 1.25 g of 2-aminothiophenol in 5 ml of ether. After stirring for 1 hour at 25°, the reaction mixture was evaporated. The residue was purified by flash chromatography on silica gel using 2% ethyl acetate in benzene as eluent. There was thus obtained 860 mg of the title compound as dark blue plates, m.p. 137°–141°.

Analysis, calculated: C, 73.81; H, 7.12; N, 4.30; S, 9.85 Observed: C, 73.77; H, 7.33; N, 4.33; S, 9.85.

EXAMPLE 37

4-Bromo-1,7-dimethoxy-3-H-phenothiazin-3-one

To a suspension of 1,7-dimethoxy-3H-phenothiazin-3-one (300 mg) in acetic acid (9 ml) was added a 0.63M solution of $Br_2$ in acetic acid (1.92 ml). After 15 minutes, methanol was added and the solid filtered, washed with ether and air dried to afford the title compound (353 mg), m.p. 267°–270° C. (dec).

EXAMPLE 38

4-Chloro-1,7-dimethoxy-3H-phenothiazin-3-one and 2,4-dichloro-1,7-dimethoxy-3-H-phenothiazin-3-one To a suspension of 1,7-dimethoxy-3H-phenothiazin-3-one (800 mg) in acetic acid (24 ml) was added a 1.15M solution of $Cl_2$ in acetic acid (3.1 ml). After 15 minutes, methanol was added and the mixture was filtered, washed with ether and air dried to afford a mixture of the two title compounds (700 mg), which were separated on a silica gel column (EtOAc:CH$_2$Cl$_2$, 1:9), affording 4-chloro-1,7-dimethoxy-3H-phenothiazin-3-one, m.p. 278°–280° C. (dec.)

Analysis, Calculated: C, 54.64; H, 3.28; N, 4.55; S, 10.42; Cl, 11.52. Observed: C, 54.44; H, 3.26; N, 4.62; S, 10.54; Cl, 11.48.

2,4-dichloro-1,7-dimethoxy-3H-phenothiazin-3-one, m.p. 259°–260° C. (dec.) m/e 341.

EXAMPLE 39

7-Methoxy-2-(4-methylpiperazin-1-yl)-3H-phenothiazine-3-one

A mixture of 7-methoxy-3H-phenothiazin-3-one (1.2 g) and N-methyl piperazine HCl (3.4 g) in DMF (20 ml) was heated at 100° C. for 3 hours. Then NaIO$_4$ (1 g) was added and the reaction mixture was heated at 100° C. for 1 hour. Ice-water was added to the reaction mixture followed by ethyl acetate. The aqueous layer was decanted, filtered and the filtrate basified with K$_2$CO$_3$ and extracted with ethyl acetate. The organic layer was evaporated to dryness, the resulting residue was dissolved in CH$_2$Cl$_2$, dried and evaporated to dryness to afford the crude final product (1.2 g) which was purified by chromatography on silica gel column eluting with 10% MEOH/CH$_2$Cl$_2$ to give the title compound, m.p. 208°–209°.

EXAMPLE 40

4-Bromo-7-methoxy-2-(4-methylpiperazin-1-yl)-3H-phenothiazin-3-one

To a suspension of 7-methoxy-2-(4-methylpiperazin-1-yl)-3H-phenothiazin-3-one (500 mg) in acetic acid (10 ml) was added a solution of bromine in acetic acid (0.5M) (6 ml) and stirred for 5 minutes. Hexane (100 ml) was added and the resulting precipitate was filtered. The solid was suspended in a mixture of aqueous K$_2$CO$_3$ (50 ml), EtOAc (100 ml) and methanol (20 ml) and stirred for 15 minutes. After filtration and decantation, the organic layer was washed with brine, dried and evaporated to dryness to afford the title compound (190 mg) m.p. 209°–210° (dec.).

EXAMPLE 41

4-Bromo-2,7-dimethoxy-3H-phenothiazin-3-one-5,5-dioxide

STEP 1

4-Bromo-3-hydroxy-2,7-dimethoxy-10-H-phenothiazine

To a suspension of 4-bromo-2,7-dimethoxy-3H-phenothiazin-3-one (100 g) in a mixture of ethyl acetate (2 l) and water (1 l) was added sodium hydrosulfite (200 g) in one batch with mechanical stirring. The orange reaction mixture was stirred for 15 hours under a nitrogen atmosphere. The resulting white reaction mixture was filtered and the precipitate washed with water under a nitrogen atmosphere to prevent air oxidation of the compound. The title compound (130 g) was obtained as a wet material and was used as such in the next step (Step 2). An analytical sample was air dried, m.p. 185° C.

Analysis, Calculated: C, 47.47; H, 3.42; N, 3.95; S, 9.05; Br, 22.56. Observed: C, 47.21; H, 3.39; N, 3.74; S, 8.76; Br, 22.44.

STEP 2

3-Acetoxy-4-bromo-2,7-dimethoxy-10-H-phenothiazine

Wet 4-bromo-3-hydroxy-2,7-dimethoxy-10-H-phenothiazine (130 g) (from step 1) was suspended in pyridine (230 ml). The mixture was cooled to 0° C. in an ice-water bath. Acetic anhydride (195 ml) was then slowly added. The solution was left stirring at room temperature for ½ hour. The mixture was then concentrated under reduced pressure to approximately ⅓ of the original volume. The a mixture of ether:hexane, 1:1 (700 ml) was added, causing a large amount of crystals to appear. These crystals were filtered, washed with ether, and air dried, giving 51.4 g of pure 3-acetoxy-4-bromo-2,7-dimethoxy-10-phenothiazine. The mother liquors were reevaporated, and ether and hexane were added again, giving 36.37 of crude 3-acetoxy-4-bromo-2,7-dimethoxy-10H-phenothiazine m.p. 201°–203° C.

Analysis, Calculated: C, 48.50; H, 3.56; N, 3.53; S, 8.09. Observed: C, 48.31; H, 3.47; N, 3.47; S, 8.00.

STEP 3

3-Acetoxy-4-bromo-2,7-dimethoxy-10H-phenothiazin-5,5-dioxide

To 3-acetoxy-4-bromo-2,7-dimethoxy-10H-phenothiazin (20 g) (from Step 2) in suspension in CH$_2$Cl$_2$:MeOH, (1:1) (500 ml), was added m-chloroperoxybenzoic acid (26.0 g). The reaction mixture rapidly became deep brown with the formation of a yellowish precipitate which corresponded to the intermediate sulfoxide on the 5-position. The mixture was heated at reflux for 18 hours. The solid was then filtered and washed with ether. Since there was still some sulfoxide remaining, the solid was suspended in ethanol:1,2-dichloroethane (500 ml) with 1.35 g of m-chloroperoxybenzoic acid and heated at reflux overnight (15 hours). The solid was then filtered and washed with ether and air dried giving 13.0 g of 3-acetoxy-4-bromo-2,7-dimethoxy-10H-phenothiazine-5,5-dioxide, m.p. 260° C.

Analysis, Calculated: C, 44.87; H, 3.29; N, 3.27; S, 7.49 Observed: C, 44.82; H, 3.21; N, 3.18; S, 7.67.

STEP 4

4-Bromo-3-hydroxy-2,7-dimethoxy-10H-phenothiazin-5,5-dioxide

To a suspension of 3-acetoxy-4-bromo-2,7-dimethoxy-10H-phenothiazine-5,5-dioxide (10.0 g) in methanol (105 ml) was added a solution of 2N aqueous sodium hydroxide (74 ml) under a nitrogen atmosphere. After 20 minutes, the mixture was acidified with 10% v/v aqueous acetic acid (250 ml), causing a large amount of compound to precipitate. The mixture was then diluted with water (105 ml) and the solid filtered, washed with water and ether and dried in a dessicator to afford quantitatively the title compound, m.p. 252°–260° C. (dec).

STEP 5

4-Bromo-2,7-dimethoxy-3H-phenothiazin-3-one-5,5-dioxide

To a stirred suspension of 4-bromo-3-hydroxy-2,7-dimethoxy-10H-phenothiazin-5,5-dioxide (from Step 4) (1 g) in THF (10 ml) was added 2,3-dichloro-5,6-dicyano-1,4-benzoquinone (1.17 g). After 15 minutes, the mixture was filtered, the solid washed with ether and air dried. The solid was filtered through a silica gel pad with CH$_2$Cl$_2$:EtOAc, 1:1, to afford the title compound (300 mg), m.p. 228°–230° C. (dec), m/e 383.

EXAMPLE 42

2,7-Dimethoxy-4-(4-methylpiperazin-1-yl)-3H-phenothazin-3-one-5,5-dioxide

To a stirred suspension of 4-bromo-3-hydroxy-2,7-dimethoxy-10H-phenothiazine-5,5-dioxide (1 g) in THF (10 ml) was added 2,3-dichloro-5,6-dicyano-1,4-benzoquinone (1.17 g). After a period of 20 minutes, N-methyl piperazine (1.44 ml) was slowly added. After 20 minutes, hexane was added to the mixture and the resulting precipitate was filtered, washed with ether and air dried. The compound was chromatographed using CH$_2$Cl$_2$:MeOH (9.5:0.5) as eluant, to afford the title compound (242 mg), m.p. 261° C. (dec.)

Analysis; Calculated: C, 58.67; H. 5.83; N, 10.80; S, 8.24 Observed: C, 58.73; H, 5.67; N, 10.83; S, 8.56

EXAMPLE 43

4-Hydroxy-2,7-dimethoxy-3H-phenothiazin-3-one-5,5-dioxide

To a stirred suspension of 4-bromo-3-hydroxy-2,7-dimethoxy-10H-phenothiazine-5,5-dioxide (100 mg) in THF (10 ml) was added water (0.1 ml) and 2,3-dichloro-5,6-dicyano-1,4-benzoquinone (0.12 g). After 20 minutes, hexane was added and the solid was filtered, washed with ether and air dried to afford the title compound, m.p. 333°–335° C. (dec.)

EXAMPLE 44

1,4-Bis(1-propylamino)-3H-phenothiazin-3-one-5,5-dioxide

To a solution of 3-hydroxy-10H-phenothiazine-5,5-dioxide (989 mg) in THF (50 ml) was added 2,3-dichloro-5,6-dicyano-1,4-benzoquinone (1.82 g). The resulting green mixture was stirred at room temperature for 3 minutes, then there was added n-propyl amine (2.36 g). The mixture was stirred for 20 minutes and then filtered. The filtrate was evaporated to dryness and the residue chromatographed on a column of silica gel eluting with a 1:20 mixture of ethyl acetate and dichloromethane to afford the title compound as a purple solid (850 mg). Crystallization from methanol afforded purple crystals (606 mg), m.p. 174°–176° C.

Analysis, Calc'd: C, 60.14; H, 5.89; N, 11.69; S, 8.92. Found: C, 60.08, H, 5.93; N, 11.80; S, 8.71.

EXAMPLE 45

1,4-Bis(4-methylpiperazin-1-yl)-3H-phenothiazine-3-one-5,5-dioxide

The procedure of Example 44 was used, substituting N-methyl piperazine for n-propyl amine to afford the title compound. It was crystallized from a toluene-hexane mixture to afford red crystals, mp: 247°–249° C. (dec).

Analysis, Calc'd: C, 59.84; H, 6.16; N, 15.86; S, 7.26 Found: C, 59.98, H, 6.35; N, 15.58; S, 7.1.

EXAMPLE 46

6-(1-Propylamino)-5H-benzo[a]phenothiazin-5-one-7,7-dioxide

STEP 1

5-acetoxy-12H-benzo[a]phenothiazine

To a stirred solution of 5-hydroxy-12H-benzo[a]phenothiazine (50 g) in pyridine (115 ml) was added acetic anhydride (48 ml). The reaction was exothermic stirring was continued without cooling for 30 minutes, then the mixture was cooled to 10° C. using an ice bath. The yellow crystalline solid was filtered and washed with ether to afford the title compound (23.4 g). The product was crystallized from ethyl acetate, m.p. 185°–186° C.

STEP 2

5-acetoxy-12H-benzo[a]phenothiazine-7,7-dioxide

To a suspension of 5-acetoxy-12H-benzo[a]phenothiazine (10 g) in dichloromethane (125 ml), was added a solution of m-chloroperoxybenzoic acid (18 g) in methanol (125 ml). The mixture was refluxed for 2.5 hours, then after cooling to room temperature the insoluble solid was filtered to afford the desired sulfone (8.6 g). The solid was recrystallized from THF m.p. 284°–287° C.

Analysis, Calc'd: C, 63.70; H, 3.86; N, 4.13; S, 9.45. Found: C, 63.67; H, 3.82; N, 4.20; S, 9.44

STEP 3

5-hydroxy-12H-benzo[a]phenothiazine-7,7 dioxide

To a suspension of 5-acetoxy-12H-benzo[a]phenothiazine-7,7-dioxide (6.6 g) in methanol (200 ml), kept under a nitrogen atmosphere was added 2N aqueous sodium hydroxide solution (132 ml). The mixture was stirred at room temperature for 7 minutes, then there was added 10% acetic acid (200 ml) and water (300 ml). After 10 minutes of stirring the mixture was filtered to afford the title compound (5.68 g) as a pink solid. The solid was recrystallized from THF, m.p. 334° C. (dec).

Calc'd: C, 63.70; H, 3.86; N, 4.13; S, 9.45. Found: C, 63.67, H, 3.82; N, 4.20; S, 9.44.

STEP 4

6-(1-Propyl amino)-5H-benzo[a]phenothiazin-5-one-7,7-dioxide

To a suspension of 5-hydroxy-12H-benzo[a]phenothiazine-7,7-dioxide (594 mg) in THF (10 ml) was added 2,3-dichloro 5,6-dicyano-1,4-benzoquinone (1.021 gram). The mixture was stirred at room temperature for 2 minutes, then there was added n-propyl amine (0.2 ml). The stirring was continued for 0.5 hour, then the mixture was evaporated to dryness. To the residue was added 50 ml dichloromethane and the mixture was stirred for 15 minutes and filtered. The filtrate was evaporated to dryness and the residue crystallized from a mixture of toluene and hexane to afford the title compound (442 mg) as a red-brown crystalline solid, m.p. 149°–151° C. (dec.).

Analysis, Calc'd: C, 64.75; H, 4.58; N, 7.95; S, 9.10. Found: C, 64.66; H, 4.48; N, 7.95; S, 9.04.

EXAMPLE 47

6-(4-Methyl piperazin-1-yl)-5H-benzo[a]phenothiazin-5-one-7,7-dioxide

The procedure of Example 46, Step 4 was used, substituting N-methyl piperazine for n-propyl amine, to afford the title compound, m.p. slow dec. from 183° C.

Analysis, Calc'd: C, 64.10; H, 4.87; N, 10.68; S, 8.15. Found: C, 63.89, H, 4.90; N, 10.56; S, 8.10.

EXAMPLE 48

6-Amino-5H-benzo[a]phenothiazin-5-one-7,7-dioxide

The procedure of Example 46, Step 4 was used, substituting 28% aqueous ammonium hydroxide solution for n-propyl amine, to afford the title compound, m.p. 264°–266° C.

Certain of the compounds herein disclosed contain one or more centers of asymmetry. The present invention is meant to include the various diastereomers of such compounds as well as their racemic and optically active resolved forms.

Some of the compounds described may exist in one or more tautomeric forms. All such tautomeric forms are included within the present invention.

What is claimed is:

1. The compounds of the Formula:

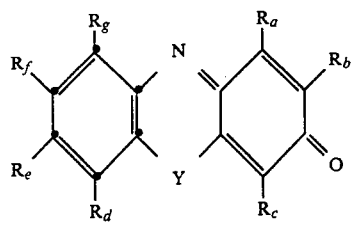

wherein the substituents are:

| Y | $R_a$ | $R_b$ | $R_c$ |
|---|---|---|---|
| S | H | $SCH_3$ | H |
| S | H | H | $SCF_3$ |
| S | H | H | CHO |
| S | H | H | $COCF_3$ |
| S | H | H | H |
| S | H | H | H |
| S | H | H | H |
| S | H | H | H |
| S | H | H | H |
| S | H | H | Cl |
| S | H | H | Cl |
| S | H | H | Cl |
| S | H | H | Cl |
| S | H | H | Cl |
| S | H | O—benzyl | Cl |
| S | H | OEt | Cl |
| S | H | OEt | Cl |
| S | $CH_3$ | H | Cl |
| S | H | $CH_3$ | Cl |
| S | H | OMe | Br |
| S | H | OMe | Cl |
| S | H | OEt | Br |
| S | H | OEt | Cl |
| S | H | OMe | Cl |
| S | H | OMe | H |
| O | H | OMe | Br |
| O | H | OMe | Cl |
| S | H | OMe | Br |
| $SO_2$ | H | H | OH |
| $SO_2$ | H | OMe | OH |
| $SO_2$ | OMe | OMe | Me |
| $SO_2$ | H | H | OMe |
| $SO_2$ | H | OMe | OMe |
| S | $OCH_3$ | $OCH_3$ | Me |
| S | H | H | $COCH_3$ |
| S | $OCH_3$ | H | Br |
| S | $OCH_3$ | Cl | Cl |
| S | $OCH_3$ | H | Cl |
| S | H | 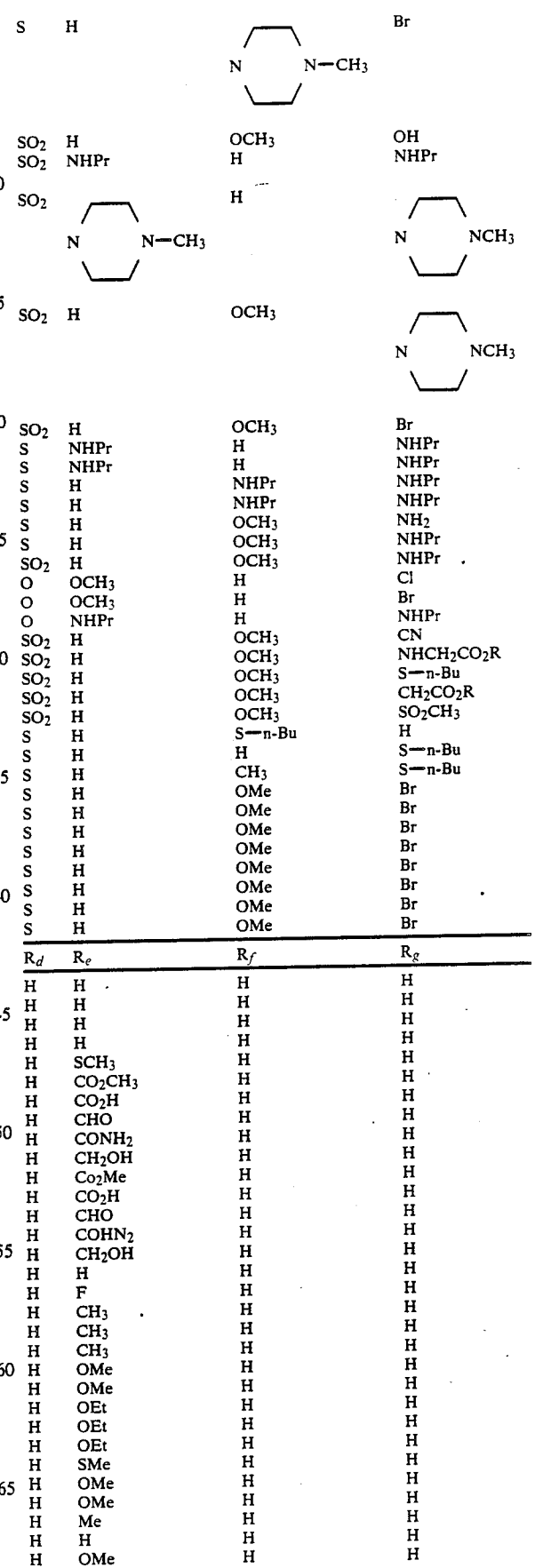 | H |
| S | H | | Br |
| $SO_2$ | H | $OCH_3$ | OH |
| $SO_2$ | NHPr | H | NHPr |
| $SO_2$ | | H | |
| $SO_2$ | H | $OCH_3$ | |
| $SO_2$ | H | $OCH_3$ | Br |
| S | NHPr | H | NHPr |
| S | NHPr | H | NHPr |
| S | H | NHPr | NHPr |
| S | H | NHPr | NHPr |
| S | H | $OCH_3$ | $NH_2$ |
| S | H | $OCH_3$ | NHPr |
| $SO_2$ | H | $OCH_3$ | NHPr |
| O | $OCH_3$ | H | Cl |
| O | $OCH_3$ | H | Br |
| O | NHPr | H | NHPr |
| $SO_2$ | H | $OCH_3$ | CN |
| $SO_2$ | H | $OCH_3$ | $NHCH_2CO_2R$ |
| $SO_2$ | H | $OCH_3$ | S—n-Bu |
| $SO_2$ | H | $OCH_3$ | $CH_2CO_2R$ |
| $SO_2$ | H | $OCH_3$ | $SO_2CH_3$ |
| S | H | S—n-Bu | H |
| S | H | H | S—n-Bu |
| S | H | $CH_3$ | S—n-Bu |
| S | H | OMe | Br |
| S | H | OMe | Br |
| S | H | OMe | Br |
| S | H | OMe | Br |
| S | H | OMe | Br |
| S | H | OMe | Br |
| S | H | OMe | Br |
| S | H | OMe | Br |

| $R_d$ | $R_e$ | $R_f$ | $R_g$ |
|---|---|---|---|
| H | H | H | H |
| H | H | H | H |
| H | H | H | H |
| H | $SCH_3$ | H | H |
| H | $CO_2CH_3$ | H | H |
| H | $CO_2H$ | H | H |
| H | CHO | H | H |
| H | $CONH_2$ | H | H |
| H | $CH_2OH$ | H | H |
| H | $Co_2Me$ | H | H |
| H | $CO_2H$ | H | H |
| H | CHO | H | H |
| H | $COHN_2$ | H | H |
| H | $CH_2OH$ | H | H |
| H | H | H | H |
| H | F | H | H |
| H | $CH_3$ | H | H |
| H | $CH_3$ | H | H |
| H | $CH_3$ | H | H |
| H | OMe | H | H |
| H | OMe | H | H |
| H | OEt | H | H |
| H | OEt | H | H |
| H | OEt | H | H |
| H | SMe | H | H |
| H | OMe | H | H |
| H | OMe | H | H |
| H | Me | H | H |
| H | H | H | H |
| H | OMe | H | H |

-continued

| | | | |
|---|---|---|---|
| H | H | H | H |
| H | H | H | H |
| H | OMe | H | H |
| H | H | H | H |
| H | H | H | H |
| H | OCH3 | H | H |
| H | OCH3 | H | H |
| H | OCH3 | H | H |
| H | OCH3 | H | H |
| H | OCH3 | H | H |
| H | OCH3 | H | H |
| H | H | H | H |
| H | H | H | H |
| H | OCH3 | H | H |
| H | OCH3 | H | H |
| H | H | H | H |
| H | OCH3 | H | H |
| H | H | H | H |
| H | OCH3 | H | H |
| H | OCH3 | H | H |
| H | OCH3 | H | H |
| H | OCH3 | H | H |
| H | OCH3 | H | H |
| H | OCH3 | H | H |
| H | H | H | H |
| H | OCH3 | H | H |
| H | OCH3 | H | H |
| H | OCH3 | H | H |
| H | OCH3 | H | H |
| H | OCH3 | H | H |
| H | H | H | H |
| H | H | H | H |
| H | H | H | H |
| H | CF3 | H | H |
| H | F | H | H |
| H | Cl | H | H |
| H | Br | H | H |
| H | NMe2 | H | H |
| H | SMe | H | H |
| H | SO2Me | H | H |
| H | Ph | H | H | and R is H or C2 to C4 alkyl.

2. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | OMe | Br | H | OMe | H | H |
| S | H | OMe | Cl | H | OMe | H | H |
| S | H | OEt | Br | H | OEt | H | H |
| S | H | OEt | Cl | H | OEt | H | H |
| S | H | OMe | Cl | H | OEt | H | H. |

3. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | OCH3 | H | Br | H | OCH3 | H | H |
| S | OCH3 | Cl | Cl | H | OCH3 | H | H |
| S | OCH3 | H | Cl | H | OCH3 | H | H. |

4. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| O | H | OMe | Br | H | OMe | H | H |
| O | H | OMe | Cl | H | OMe | H | H. |

5. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| O | OCH3 | H | Cl | H | OCH3 | H | H |
| O | OCH3 | H | Br | H | OCH3 | H | H. |

6. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | SCH3 | H | H | H | H | H |
| S | H | H | H | H | SCH3 | H | H |
| S | H | OMe | H | H | SMe | H | H |
| S | H | S—n-Bu | H | H | H | H | H |
| S | H | H | S—n-Bu | H | H | H | H |
| S | H | CH3 | S—n-Bu | H | H | H | H |
| S | H | OMe | Br | H | SMe | H | H |
| S | H | OMe | Br | H | SO2Me | H | H. |

7. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | H | H | H | CO2CH3 | H | H |
| S | H | H | H | H | CO2H | H | H |
| S | H | H | H | H | CONH2 | H | H |
| S | H | H | Cl | H | CO2Me | H | H |
| S | H | H | Cl | H | CO2H | H | H |
| S | H | H | Cl | H | CONH2 | H | H |
| SO2 | H | OCH3 | CH2CO2R | H | OCH3 | H | H. |

8. A compound of claim 1 wherein the substituents are:

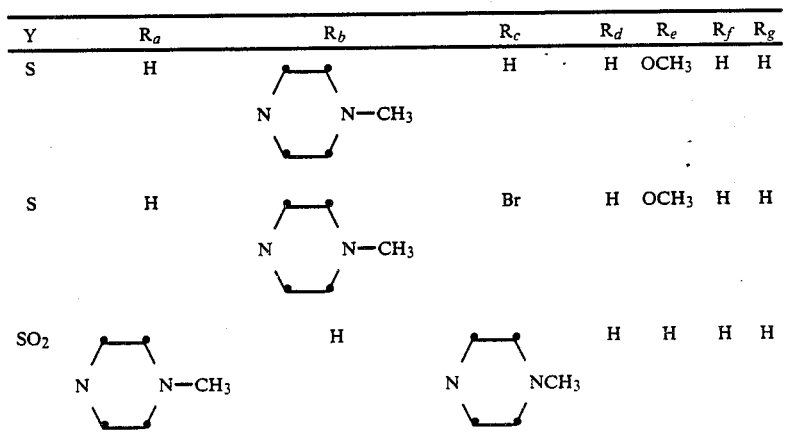

-continued

| Y | $R_a$ | $R_b$ | $R_c$ | $R_d$ | $R_e$ | $R_f$ | $R_g$ |
|---|---|---|---|---|---|---|---|
| $SO_2$ | H | $OCH_3$ | 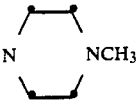 | | H | $OCH_3$ | H | H. |

9. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | $OCH_3$ | $NH_2$ | H | $OCH_3$ | H | H |
| S | H | $OCH_3$ | NHPr | H | $OCH_3$ | H | H |
| $SO_2$ | H | $OCH_3$ | $NHCH_2CO_2R$ | H | $OCH_3$ | H | H. |

10. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | H | H | H | CHO | H | H |
| S | H | H | H | H | $CH_2OH$ | H | H |
| S | H | H | Cl | H | CHO | H | H |
| S | H | H | Cl | H | $CH_2OH$ | H | H. |

11. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | NHPr | H | NHPr | H | H | H | H |
| S | NHPr | H | NHPr | H | $OCH_3$ | H | H |
| S | H | NHPr | NHPr | H | H | H | H |
| S | H | NHPr | NHPr | H | $OCH_3$ | H | H |
| O | NHPr | H | NHPr | H | H | H | H. |

12. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | OEt | Cl | H | F | H | H |
| S | H | OEt | Cl | H | $CH_3$ | H | H |
| S | H | OMe | Br | H | Me | H | H |
| S | H | OMe | Br | H | $CF_3$ | H | H |
| S | H | OMe | Br | H | F | H | H |
| S | H | OMe | Br | H | Cl | H | H |
| S | H | OMe | Br | H | Br | H | H |
| S | H | OMe | Br | H | $NMe_2$ | H | H |
| S | H | OMe | Br | H | Ph | H | H. |

13. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| $SO_2$ | H | H | OH | H | H | H | H |
| $SO_2$ | H | OMe | OH | H | OMe | H | H |
| $SO_2$ | OMe | OMe | Me | H | H | H | H |
| $SO_2$ | H | H | OMe | H | H | H | H |
| $SO_2$ | H | OMe | OMe | H | OMe | H | H |
| $SO_2$ | H | $OCH_3$ | OH | H | $OCH_3$ | H | H |
| $SO_2$ | NHPr | H | NHPr | H | H | H | H |

| Y | $R_a$ | $R_b$ | $R_c$ | $R_d$ | $R_e$ | $R_f$ | $R_g$ |
|---|---|---|---|---|---|---|---|
| $SO_2$ | H | $OCH_3$ | Br | H | $OCH_3$ | H | H |
| $SO_2$ | H | $OCH_3$ | NHPr | H | $OCH_3$ | H | H |
| $SO_2$ | H | $OCH_3$ | CN | H | $OCH_3$ | H | H |
| $SO_2$ | H | $OCH_3$ | S—n-Bu | H | $OCH_3$ | H | H |
| $SO_2$ | H | $OCH_3$ | $SO_2CH_3$ | H | $OCH_3$ | H | H. |

14. A compound of claim 1 wherein the substituents are:

| Y | $R_a$ | $R_b$ | $R_c$ | $R_d$ | $R_e$ | $R_f$ | $R_g$ |
|---|---|---|---|---|---|---|---|
| S | H | H | CHO | H | H | H | H |
| S | H | H | $COCF_3$ | H | H | H | H |
| S | H | C—benzyl | Cl | H | H | H | H |
| S | $CH_3$ | H | Cl | H | $CH_3$ | H | H |
| S | H | $CH_3$ | Cl | H | $CH_3$ | H | H |
| S | $OCH_3$ | $OCH_3$ | Me | H | H | H | H |
| S | H | H | $COCH_3$ | H | H | H | H. |

15. The compound of claim 1 which is: 4-bromo-2,7-dimethoxy-3H-phenothiazin-3-one.

16. The compound of claim 1 which is: 4-chloro-2,7-dimethoxy-3H-phenothiazin-3-one.

17. The compound of claim 1 which is: 4-bromo-2,7-diethoxy-3H-phenothiazin-3-one.

18. The compound of claim 1 which is: 4-chloro-2,7-diethoxy-3H-phenothiazin-3-one.

19. The compound of claim 1 which is: 4-bromo-2,7-dimethoxy-3H-phenoxazin-3-one.

20. The compound of claim 1 which is: 4-chloro-2,7-dimethoxy-3H-phenoxazin-3-one.

21. The compounds of the formula:

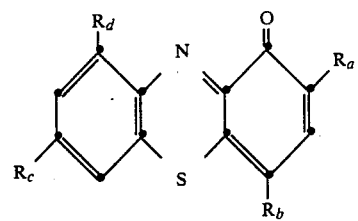

wherein the substituents are:

| $R_a$ | $R_b$ | $R_c$ | $R_d$ |
|---|---|---|---|
| t-Bu | t-Bu | H | H |
| t-Bu | F | H | H |
| t-Bu | t-Bu | Me | H |
| t-Bu | t-Bu | SMe | H |
| t-Bu | t-Bu | H | OMe. |

22. The compounds: 2-S-glutathionyl-3H-phenothiazin-3-one; and 4-chloro-2-S-glutathionyl-phenothiazin-3-one.

* * * * *